(12) United States Patent
Jacobs

(10) Patent No.: US 11,617,586 B2
(45) Date of Patent: Apr. 4, 2023

(54) GASTROESOPHAGEAL REFLUX TREATMENT SYSTEM, METHOD, AND DEVICE

(71) Applicant: Moises Jacobs, Miami, FL (US)

(72) Inventor: Moises Jacobs, Miami, FL (US)

( * ) Notice: Subject to any disclaimer, the term of this patent is extended or adjusted under 35 U.S.C. 154(b) by 43 days.

(21) Appl. No.: 16/599,954

(22) Filed: Oct. 11, 2019

(65) Prior Publication Data

US 2020/0113720 A1 Apr. 16, 2020

Related U.S. Application Data

(60) Provisional application No. 62/744,538, filed on Oct. 11, 2018.

(51) Int. Cl.
*A61F 5/00* (2006.01)
*A61B 17/12* (2006.01)
(Continued)

(52) U.S. Cl.
CPC ...... *A61B 17/12013* (2013.01); *A61F 2/0063* (2013.01); *A61F 2/04* (2013.01); *A61F 5/0036* (2013.01); *A61F 5/0079* (2013.01); *A61B 2017/00004* (2013.01); *A61B 2017/00827* (2013.01); *A61F 2002/0068* (2013.01); *A61F 2002/045* (2013.01); *A61F 2210/0004* (2013.01); *A61F 2220/0075* (2013.01); *A61F 2230/0026* (2013.01); *A61F 2230/0043* (2013.01); *A61F 2230/0052* (2013.01); *A61F 2230/0054* (2013.01); *A61F 2230/0058* (2013.01)

(58) Field of Classification Search
CPC .......... A61F 5/005–0059; A61F 5/0063–0069; A61F 5/0073–0079; A61F 5/0083–0089; A61F 5/0036; A61F 2220/0075; A61F 2/04; A61F 2/0063; A61F 2002/045; A61B 2017/00827; A61B 17/12–1285; A61B 2017/12004–1225
See application file for complete search history.

(56) References Cited

U.S. PATENT DOCUMENTS 6,572,627 B2 6/2003 Gabbay
10,130,370 B2 11/2018 Szewczyk et al.
(Continued)

FOREIGN PATENT DOCUMENTS

FR 2944432 A1 10/2010

OTHER PUBLICATIONS

International Pat. Appl. No. PCT/US2019/055879, International Search Report and Written Opinion dated Jan. 31, 2020, 14 pgs.
(Continued)

*Primary Examiner* — Jennifer Dieterle
*Assistant Examiner* — Rebecca Lynee Zimmerman
(74) *Attorney, Agent, or Firm* — Foley & Lardner LLP

(57) ABSTRACT

An improved gastroesophageal reflux preventer and related methods are provided. The improved gastroesophageal reflux preventer may include an absorbable material able to be placed in contact with a body organ and configured to induce a scarification of the body organ in response to absorption by the body organ of the material. In this manner, a proximate sphincter may be tightened, such as to ameliorate reflux through a gastroesophageal sphincter.

26 Claims, 20 Drawing Sheets

(51) Int. Cl.
    *A61F 2/00*         (2006.01)
    *A61F 2/04*         (2013.01)
    *A61B 17/00*       (2006.01)

(56) References Cited

U.S. PATENT DOCUMENTS

| | | |
|---|---|---|
| 2005/0113855 A1 | 5/2005 | Kennedy et al. |
| 2005/0216040 A1 | 9/2005 | Gertner et al. |
| 2007/0185374 A1* | 8/2007 | Kick ................ A61B 17/00234 600/37 |
| 2008/0058840 A1* | 3/2008 | Albrecht ............. A61B 17/083 606/153 |
| 2010/0240965 A1 | 9/2010 | Furuta et al. |
| 2011/0098731 A1* | 4/2011 | Whitbrook ............ A61F 2/0018 606/151 |
| 2012/0226294 A1* | 9/2012 | Tuval ................ A61B 17/0401 606/148 |
| 2014/0088342 A1* | 3/2014 | Djurovic ............... A61F 2/0036 600/30 |
| 2015/0105859 A1 | 4/2015 | Frigstad et al. |
| 2020/0113570 A1 | 4/2020 | Jacobs |

OTHER PUBLICATIONS

International Preliminary Report on Patentability for PCT/US2019/055879 dated Apr. 22, 2021, 11 pgs.
U.S. Appl. No. 16/579,501, filed Sep. 23, 2019, Gastroesophageal Reflux Treatment System, Method, and Device.
Foreign Search Report on EP 19871032.9 dated May 23, 2022.

\* cited by examiner

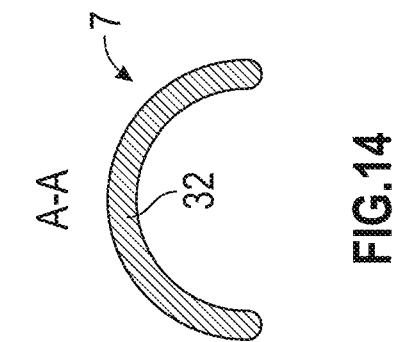
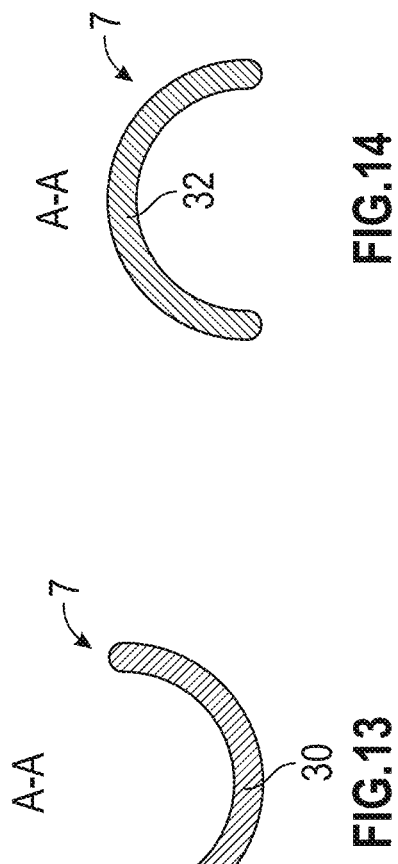
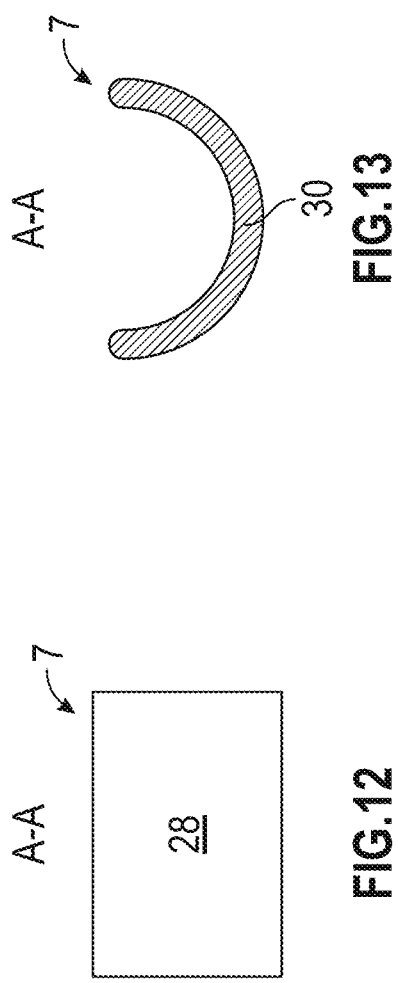
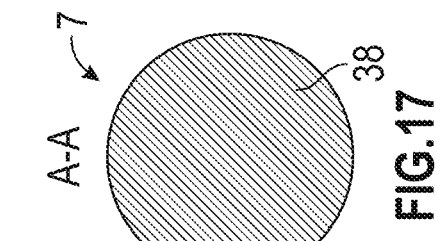
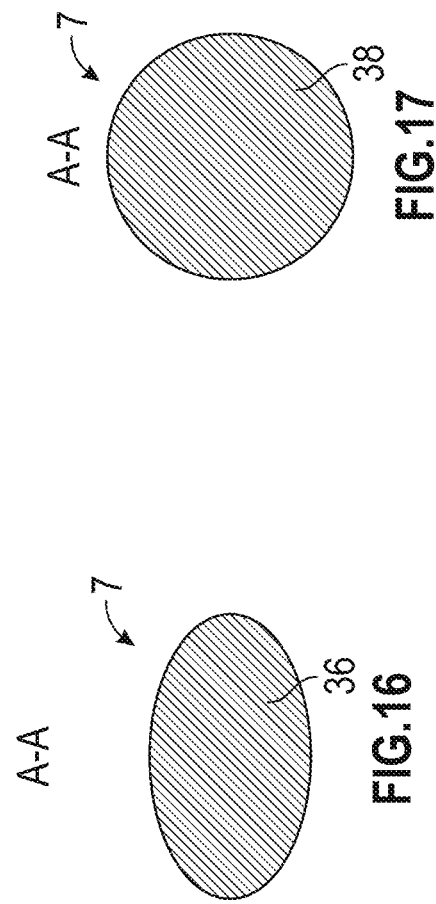

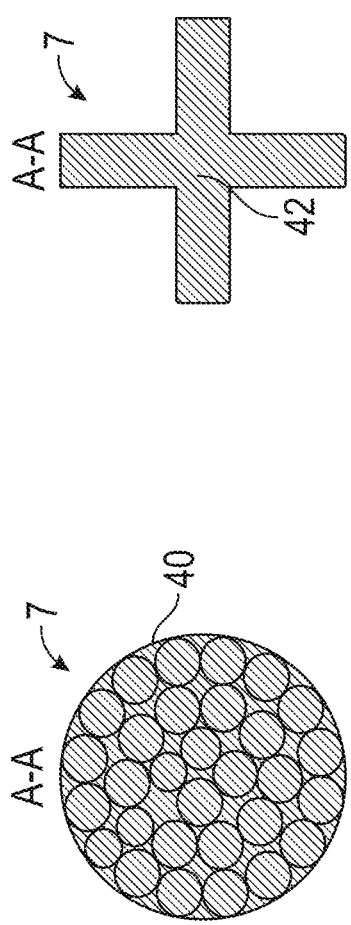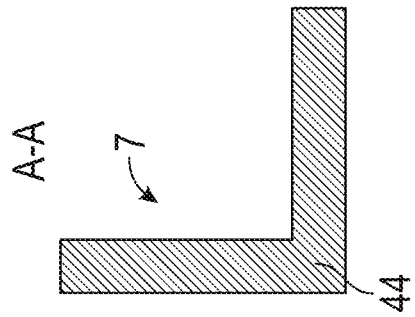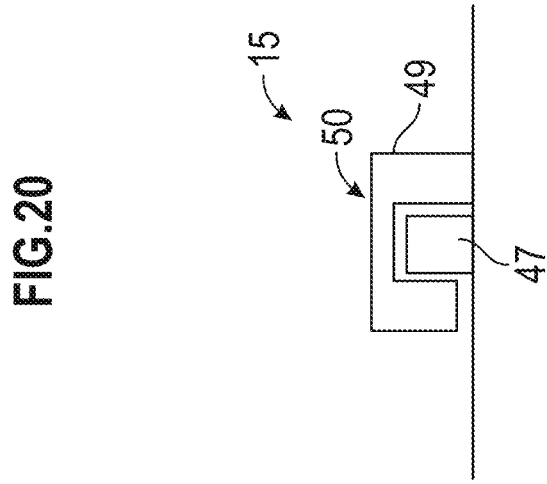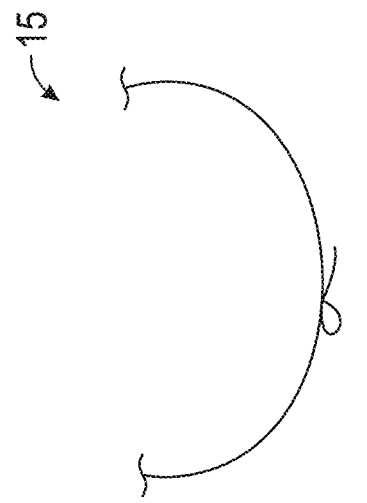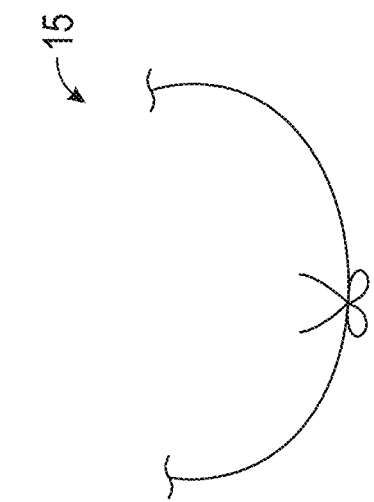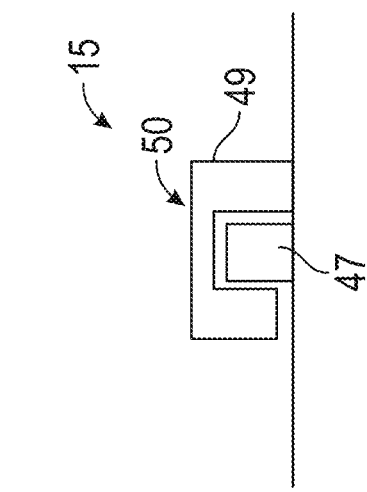

GASTROESOPHAGEAL REFLUX TREATMENT SYSTEM, METHOD, AND DEVICE

CROSS-REFERENCE TO RELATED APPLICATION(S)

This application claims priority to and the benefit of U.S. Prov. Pat. App. No. 62/744,538 entitled "GASTROESOPHAGEAL REFLUX TREATMENT SYSTEM, METHOD, AND DEVICE," naming Moises Jacobs as inventor, and filed on Oct. 11, 2018, the contents of which are hereby incorporated herein by reference in their entirety for any purpose.

FIELD

The present disclosure relates generally to a medical device, and more specifically to an improved gastroesophageal reflux treatment system, method, and device.

BACKGROUND

Many individuals suffer from gastroesophageal reflux. Efforts have been made to treat gastroesophageal reflux. Many treatment modalities exhibit significant complications, are complex, and/or are very expensive. Thus there exists a need for improved systems, methods, and devices for treatment of gastroesophageal reflux.

SUMMARY

The forgoing features and elements may be combined in various combinations without exclusivity, unless expressly indicated herein otherwise. These features and elements as well as the operation of the disclosed embodiments will become more apparent in light of the following description and accompanying drawings.

Embodiments of gastroesophageal reflux treatment systems, methods, and devices are disclosed. For instance, an implantable gastroesophageal reflux treatment device may include a gastroesophageal reflux preventer and a closure mechanism emplaceable proximate to an organ. In various embodiments, at least a portion of the gastroesophageal reflux preventer is absorbable by a human body. In various embodiments, at least a portion of the gastroesophageal reflux preventer is configured to induce a scar pattern upon absorption by the human body. By structuring the gastroesophageal reflux preventer to induce a desired scar pattern upon absorption, tightening of a sphincter may be induced responsive to the scarring, thereby ameliorating gastroesophageal reflux through the sphincter. Thus, a gastroesophageal reflux treatment system, method, and device may include the planned inducement of scarring in a pattern corresponding to a structure of a gastroesophageal reflux preventer as disclosed herein.

A gastroesophageal reflux preventer is provided. The gastroesophageal reflux preventer includes an elongate portion of an absorbable material having a first end and a second end. The gastroesophageal reflux preventer includes a support string having a first portion extending outwardly from the first end and having a second portion extending outwardly from the second end. The gastroesophageal reflux preventer also includes a closure mechanism configured to retain at least a portion of the elongate portion in contact with a body organ during at least a portion of a scarification of the body organ in response to absorption by the body organ of the elongate portion.

A further gastroesophageal reflux preventer is provided. The further gastroesophageal reflux preventer may include a plurality of nodes including pieces of an absorbable mesh material linked together by a support string. The support string may have a first portion extending outwardly from a first end of the plurality of nodes linked together and may have a second portion extending outwardly from a second end of the plurality of nodes linked together. Moreover, the gastroesophageal reflux preventer may have a closure mechanism configured to retain at least a portion of the plurality of nodes in contact with a body organ during at least a portion of a scarification of the body organ in response to absorption by the body organ of at least one node of the plurality of nodes.

A method of making a gastroesophageal reflux preventer is provided. The method may include providing an elongate portion of an absorbable material having a first end and a second end. The method may also include providing a support string having a first portion extending outwardly from the first end and having a second portion extending outwardly from the second end. The method may also include providing a closure mechanism attached to the support string and configured to retain at least a portion of the elongate portion in contact with a body organ during at least a portion of a scarification of the body organ in response to absorption by the body organ of the elongate portion.

A method of reducing leakage of a body fluid through a gastroesophageal sphincter is provided. In various embodiments, the method includes resting an elongate portion of a gastroesophageal reflux preventer against at least one of a stomach and an esophagus proximate to the gastroesophageal sphincter. The method may further include retaining at least a portion of the elongate portion in contact with the at least one of the stomach and the esophagus by encircling at least one of the elongate portion and a support string extending outwardly from the elongate portion about the at least one of the stomach and the esophagus and engaging a closure mechanism attached to the support string. In various embodiments, engaging the closure mechanism includes knotting together (i) a first portion of the support string extending outwardly from a first end of the elongate portion and (ii) a second portion of the support string extending outwardly from a second end of the elongate portion.

A further gastroesophageal reflux preventer is provided. The gastroesophageal reflux preventer may include an elongate portion and a closure mechanism. The elongate portion may be of an absorbable material having a first end and a second end. The closure mechanism may be a knotting together of the first end and the second end to retain at least a portion of the elongate portion in contact with a body organ during at least a portion of a scarification of the body organ in response to absorption by the body organ of the elongate portion.

A gastroesophageal reflux preventer is provided. The gastroesophageal reflux preventer may include an elongate portion an elongate portion of an absorbable material having a first end and a second end. The elongate portion may include a support string at least partially curved and connecting the first end and the second end and supporting the elongate portion in a curved-shape. In various embodiments, the elongate portion further includes a plurality of spaced apart nodes spaced along the support string, wherein the support string is configured to retain at least a portion of the elongate portion in contact with a body tissue during at least a portion of a scarification of the body tissue in response to absorption by the body organ of the elongate portion.

A further gastroesophageal reflux preventer is provided. The gastroesophageal reflux preventer may include a plurality of nodes including pieces of an absorbable material linked together by a support string wherein at least one node of the plurality of nodes is absorbable by a body tissue when placed in contact with the body tissue and the absorption creates scarification adjacent the contact. The support string may have a curved shape and be at least partially inelastically deformable to at least partially correspond to a shape of the body tissue, and configured to at least partially retain the pre-formed curved shape after being sutured to the body tissue.

Another gastroesophageal reflux preventer may be provided. The gastroesophageal reflux preventer may include an elongate portion of an absorbable material having a pre-formed curved shape that is at least semi-rigid and having a first end and a second end that is opposite the first end of the pre-formed curved shape.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the drawing figures, wherein like numerals denote like elements.

FIG. 12 illustrates an example gastroesophageal reflux treatment device with a cross-sectional profile corresponding to a trapezoidal cross-section, in accordance with various embodiments;

FIG. 13 illustrates an example gastroesophageal reflux treatment device with a cross-sectional profile corresponding to a concave cross-section, in accordance with various embodiments;

FIG. 14 illustrates an example gastroesophageal reflux treatment device with a cross-sectional profile corresponding to a convex cross-section, in accordance with various embodiments;

FIG. 15 illustrates an example gastroesophageal reflux treatment device with a cross-sectional profile corresponding to a flattened cross-section, in accordance with various embodiments;

FIG. 16 illustrates an example gastroesophageal reflux treatment device with a cross-sectional profile corresponding to an oval cross-section, in accordance with various embodiments;

FIG. 17 illustrates an example gastroesophageal reflux treatment device with a cross-sectional profile corresponding to an round cross-section, in accordance with various embodiments;

FIG. 18 illustrates an example gastroesophageal reflux treatment device with a cross-sectional profile corresponding to a stranded cross-section, in accordance with various embodiments;

FIG. 19 illustrates an example gastroesophageal reflux treatment device with a cross-sectional profile corresponding to a t-shape cross-section, in accordance with various embodiments;

FIG. 20 illustrates an example gastroesophageal reflux treatment device with a cross-sectional profile corresponding to an L-shape cross-section, in accordance with various embodiments;

FIG. 21 illustrates an example gastroesophageal reflux treatment device with a closure mechanism corresponding to a bow knot closure, in accordance with various embodiments;

FIG. 22 illustrates an example gastroesophageal reflux treatment device with a closure mechanism corresponding to a square knot closure, in accordance with various embodiments;

FIG. 23 illustrates an example gastroesophageal reflux treatment device with a closure mechanism corresponding to an inward clasp closure, in accordance with various embodiments;

DETAILED DESCRIPTION

Figure 1A:
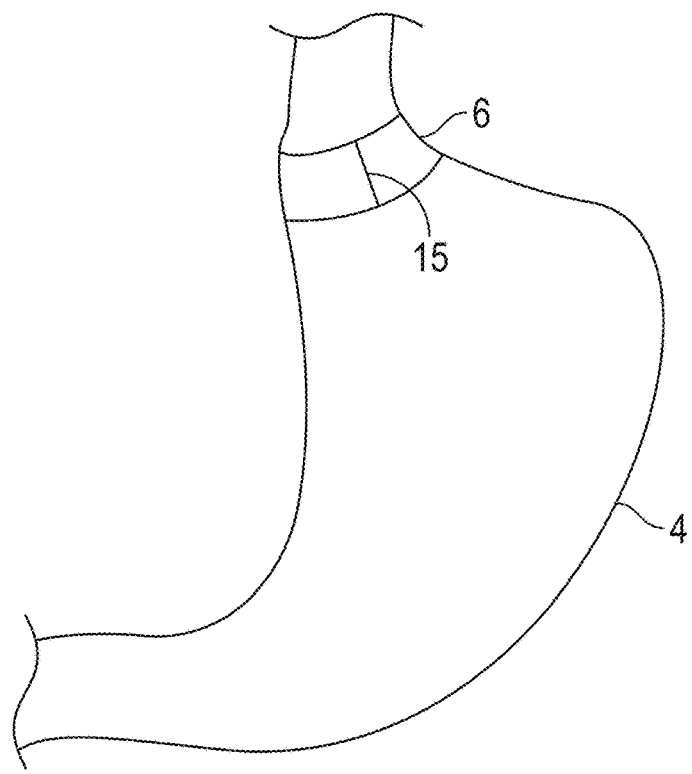
FIG. 1A illustrates a block diagram of a gastroesophageal reflux treatment device installed proximate to a gastroesophageal sphincter of a stomach and with an elongate portion extending 360 degrees around an esophagus, according to various embodiments.

The detailed description of exemplary embodiments herein makes reference to the accompanying drawings, which show exemplary embodiments by way of illustration. While these exemplary embodiments are described in sufficient detail to enable those skilled in the art to practice embodiments of the disclosure, it should be understood that other embodiments may be realized and that logical changes and adaptations in design and construction may be made in accordance with this invention and the teachings herein. Thus, the detailed description herein is presented for purposes of illustration only and not limitation. The scope of the disclosure is defined by the appended claims. For example, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

Furthermore, any reference to singular includes plural embodiments, and any reference to more than one component or step may include a singular embodiment or step. Surface shading lines may be used throughout the figures to denote different parts but not necessarily to denote the same or different materials.

In various example embodiments, a 5 mm circumference rounded solid meshed absorbable material of different lengths (e.g., 5 cm, 6 cm, 7 cm, and/or 8 cm in length, or any other desired length) with sutures protruding at each end is provided. In various instances a single suture protrudes at each end. The single sutures can be tied to each other to close a circle when placed around the gastroesophageal junction. The mesh may loosely lie around the esophagus, so that when the ends are tied, the mesh by itself does not constrict the esophagus.

In various further example embodiments, a structure of absorbable material, such as a semi-rigid structure, may be provided without protruding sutures at the ends. The structure is able to be sutured to a gastroesophageal junction or other body tissue. Tissue may be sutured over a portion of the structure. Such a structure may extend only partially about the gastroesophageal junction so that it is not necessary to tie the ends together. Such a structure may extend only partially about the gastroesophageal junction so that there is a gap at the ends. Such a structure may be placed in any orientation relative to the junction, such as resembling a horseshoe, semi-circle, arc, and/or bend pointing upwardly, downwardly, to a side, and orientations therebetween.

As used herein "semi-rigid" means a structure that is flexible so that, if in interfering relation with an organ or body tissue during emplacement, the structure may be flexibly bent to ameliorate the interfering relation, and after emplacement, the structure returns at least partially to its original shape once emplaced on an organ. "Semi-rigid" may also, in various embodiments, have meaning that encompasses a structure that may be bendable in either or both fully or partially elastic or fully or partially inelastic deformation. For example, a "semi-rigid" structure may also, in various embodiments, have meaning that encompasses a structure that is "malleable," meaning moldable or bendable to a specific shape to better fit to a specific patient's uniquely shaped anatomy. As used herein "rigid" means a structure that retains its shape such that an organ, if in interfering relation with the structure, must be distended during emplacement to ameliorate the interference. As used herein, "absorbable" may mean absorbable, partially absorbable, surroundable by tissue overgrowth, dissolvable, and/or partially dissolvable.

The absorbable material may be synthetic absorbable surgical suture, such as a monofilament prepared from a copolymer of glycolide and epsilon-caprolactone. For example, the absorbable material may be poliglecaprone 25, Monocryl® available from Ethicon, and/or the like. Moreover, the absorbable material may be a synthetic absorbable surgical suture such as may be formed of a copolymer made from 90% glycolide and 10% L-lactide. For example, the absorbable material may be polyglactin 910, Vicryl® available from Ethicon, and/or the like. In various embodiments, the absorbable material may be prepared from the polyester, poly (p-dioxanone). For example, the absorbable material may be polydioxanone, PDS® II available from Ethicon, and/or the like. One may appreciate that in further embodiments, the absorbable material may be any suitable material identified by a skilled artisan.

Alternatively, the round solid mesh may be of longer length, but it may have a hollow inner diameter through which an absorbable suture passes and slides, so that the solid mesh can be cut away/separated from the inner suture at predetermined lengths or at any desired lengths, making a "one size fits all" implantable gastroesophageal reflux treatment device for different esophageal circumferences. The protruding sutures may be loosely tied, creating a loose circle of mesh around the esophagus, and any excess suture is cut away.

In various embodiments, the implantable gastroesophageal reflux treatment device, such as the rounded solid absorbable mesh, is placed between the posterior vagus nerve and around at least a portion of the outer wall of the esophagus at the gastroesophageal junction below the diaphragm. Any hiatal hernias may be repaired if present thus returning the gastroesophageal junction to its normal anatomic position if possible, at the same time that the implantable gastroesophageal reflux treatment device is emplaced.

Subsequently, scar tissue induced by the mesh, enhances closure of the sphincter of the gastroesophageal junction as the mesh is absorbed. In this manner, reflux through the sphincter is ameliorated.

Further aspects, features, and embodiments are disclosed herein below with reference to specific drawings. For example, turning attention now to FIGS. 1A-1C, an implantable gastroesophageal reflux treatment device 1 is illustrated. The implantable gastroesophageal reflux treatment device 1 includes a gastroesophageal reflux preventer 6 and a closure mechanism 15 (FIGS. 1A-1B) emplaceable proximate to an organ, such as a stomach 4. In further embodiments, the closure mechanism 15 is omitted (FIG. 1C) and the implantable gastroesophageal reflux treatment device 1 is sutured to the organ and does not encircle the organ. Such an implantable gastroesophageal reflux treatment device 1 may be semi-rigid so that it may retain an approximate horseshoe shape and/or an approximate semicircular and/or an arcuate shape. The gastroesophageal reflux preventer 6 may be an elongate portion of absorbable material that is retained in place by the closure mechanism 15 and/or by rigidity and/or semi-rigidity for at least a period of time during which at least a portion of the gastroesophageal reflux preventer 6 dissolves and/or is absorbed by the body. Unexpectedly, a resultant scar induced proximate to the area of contact by the gastroesophageal reflux preventer 6 against the stomach 4 causes tightening of the stomach 4 in the area of the resultant scar, improving functioning of a sphincter. The elongate portion may be positioned to at least partially encircle an esophagus at or near the junction of the esophagus to the stomach, so that the resultant scar is proximate to the gastroesophageal sphincter.

Figure 1B:
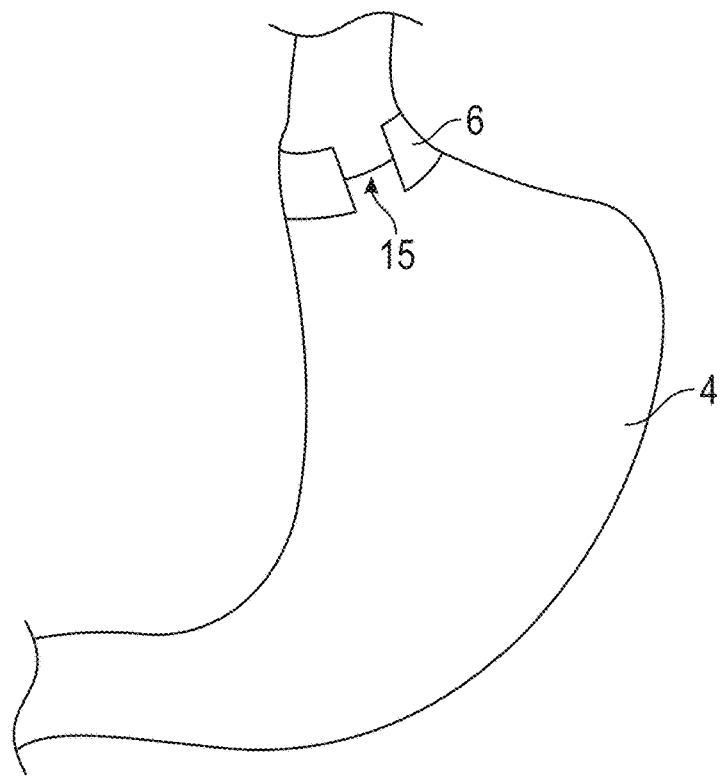
FIGS. 1B-1C illustrate block diagrams of gastroesophageal reflux treatment devices installed proximate to a gastroesophageal sphincter of a stomach and with an elongate portion extending less than 360 degrees around an esophagus, for example, 270 degrees, 180 degrees, or less than 270 degrees, or less than 180 degrees, according to various embodiments.
Figure 1C:
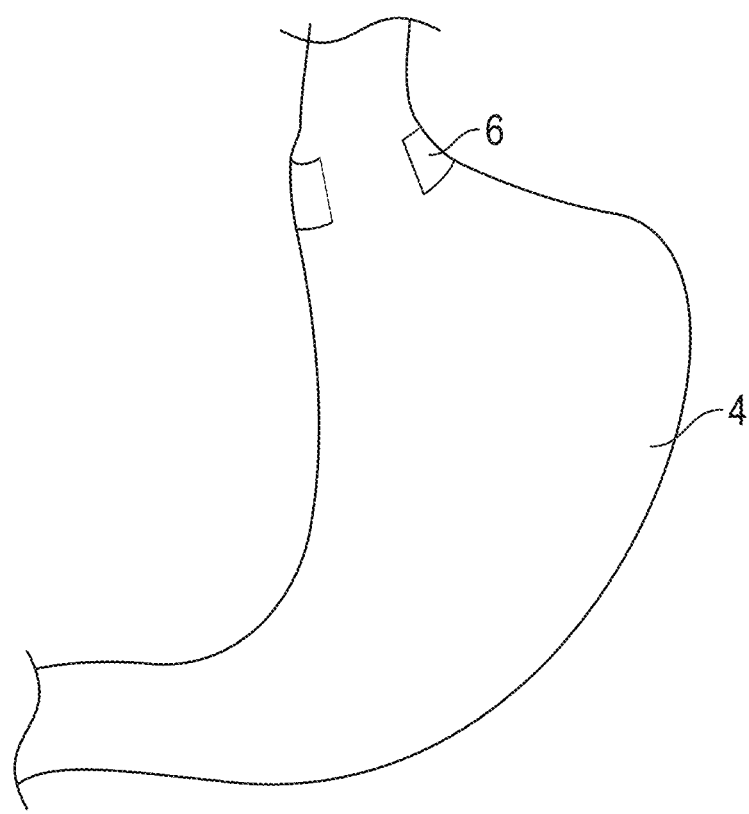

In various embodiments, the resultant scar induced proximate to the area of contact has a size and shape (a profile) carefully tuned by tuning of the geometry of the gastroesophageal reflux preventer. For instance, a scar may be 360 degrees around an esophagus, such as may be generated by a gastroesophageal reflux preventer 6 shown in FIG. 1A, or may be less than 360 degrees around an esophagus, such as may be generated by a gastroesophageal reflux preventer 6 shown in FIGS. 1B-1C. For instance, in various instances, the gastroesophageal reflux preventer 6 may have an elongate portion extending 270 degrees or 180 degrees, or less than 270 degrees, or less than 180 degrees or another length less than 360 degrees around an esophagus, as shown in FIGS. 1B-1C. In further instances, the gastroesophageal reflux preventer 6 may have an elongate portion extending 360 degrees around the esophagus, as shown in FIG. 1A. A scar may be continuous, or may be discontinuous. The size, shape, and spacing of the local scar segments of a discontinuous scar may be set according to a scarring profile of beads, sections, or other features of the gastroesophageal reflux preventer 6. For instance, reduced esophageal motility may be caused by acid over time stiffening an esophagus. For a patient with reduced esophageal motility, a continuous 360 degree scar encircling the esophagus may excessively tighten the gastroesophageal sphincter, or otherwise be non-recommended. Thus, scar profiles may be tailored from patient to patient.

The implantable gastroesophageal reflux treatment device 1 may have a variety of configurations. For instance, different gastroesophageal reflux preventers 6 may combine with different closure mechanisms 15 or no closure mechanism 15 at all, rather being supported by suturing and/or rigidity and/or semi-rigidity. Various configurations of gastroesophageal reflux preventers 6 may have different cross-sectional profiles 7, such as those shown in FIGS. 12-20. Various configurations of closure mechanisms 15 may include embodiments such as those shown in FIGS. 21-25.

The gastroesophageal reflux preventers 6 may include a variety of configurations of absorbable materials and also include a support string 3. The support string 3 may comprise a string made of absorbable material, such as an absorbable suture. The support string 3 may extend from the ends of the various gastroesophageal reflux preventers 6 discussed herein. The support string 3 may be connectable to itself such as via a closure mechanism 15. For example, the support string 3 extending from one end may be tied with the support string 3 extending from the other end into a knot. In various instances, the support string 3 passes through device, for instance, through an elongate portion of absorbable material, and extends from each end. In further instances, the support string 3 comprises two segments, with a first segment attached to a first end of the device (e.g., to an elongate portion of absorbable material) and a second segment attached to a second end of the device (e.g., to the elongate portion of absorbable material). Moreover, while reference is made to a support string 3 throughout, such reference is for convenience, and in various embodiments, the support string 3 is a shorthand description of a portion of the elongate portion aspect of the gastroesophageal reflux preventer 6. For instance, rather than knotting an outwardly extending support string 3 to retain the gastroesophageal reflux preventer 6, the support string 3 may be a shorthand description for knotting together the ends of the elongate portion of the gastroesophageal reflux preventer 6, and no separate string aspect may be provided. For further example, the support string 3 may be a rigid or semi-rigid feature of the gastroesophageal reflux preventer 6, supporting the gastroesophageal reflux preventer 6 in a horseshoe, semi-circular, and/or arcuate shape. Moreover, the support string 3 may be a shorthand description of a semi-rigid or rigid characteristic of a different part of the gastroesophageal reflux preventer 6 and not a separate structure thereof.

Figure 2:
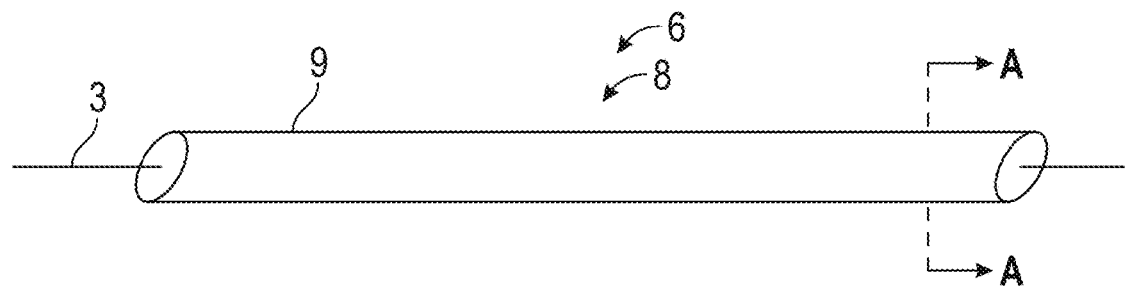
FIG. 2 illustrates an example gastroesophageal reflux treatment device having a sheathed preventer, in accordance with various embodiments.
Figure 3:
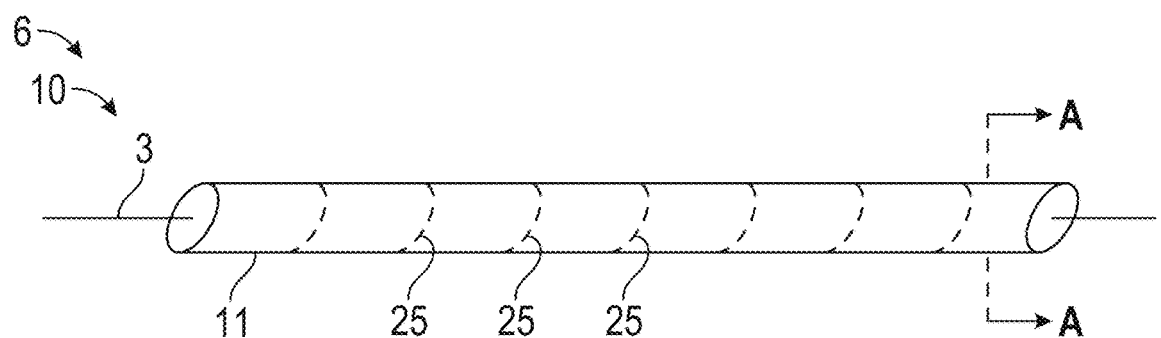
FIG. 3 illustrates an example gastroesophageal reflux treatment device having a perforated sheathed preventer, in accordance with various embodiments.
Figure 4:
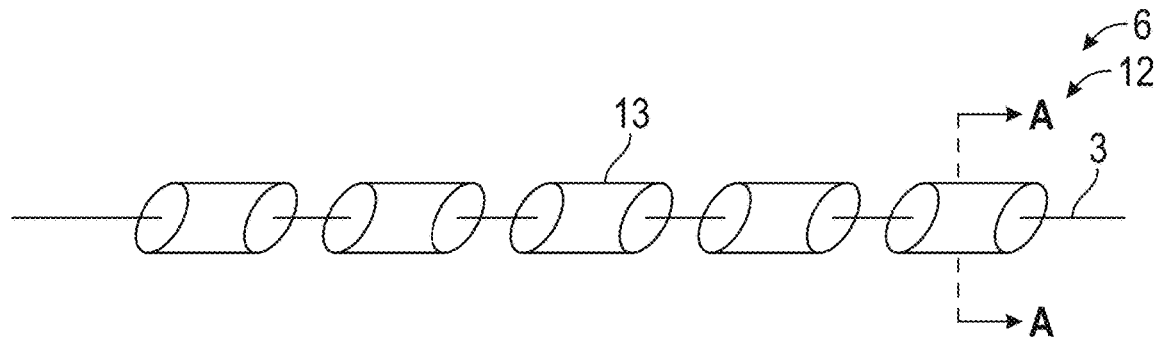
FIG. 4 illustrates an example gastroesophageal reflux treatment device having a sectioned sheathed preventer, in accordance with various embodiments.
Figure 5:
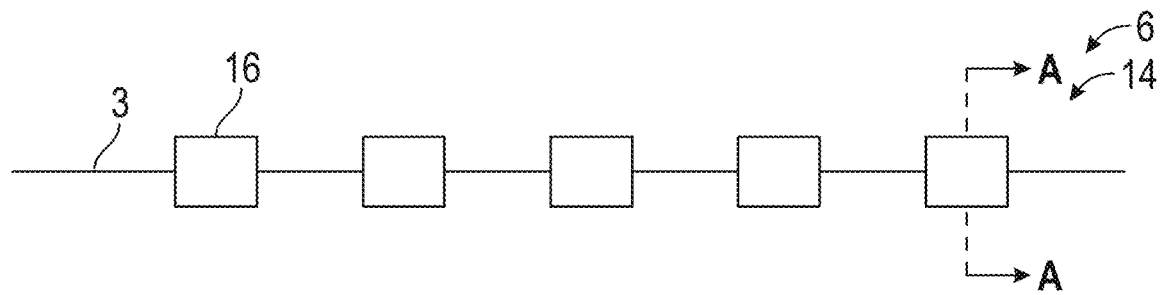
FIG. 5 illustrates an example gastroesophageal reflux treatment device having an embodiment of a linked node preventer with trapezoidal nodes, in accordance with various embodiments.

With specific attention now to FIGS. 2-11, 41, 42, and 43A-C various embodiments of gastroesophageal reflux preventers 6 are now discussed. For instance, FIG. 2 depicts a gastroesophageal reflux preventer 6 comprising an elongate portion configured as a sheathed preventer 8. A sheathed preventer 8 may include a tubular portion 9. A tubular portion 9 may comprise a tube made from an absorbable material. In various embodiments, the tubular portion 9 comprises a 5 mm circumference rounded solid meshed absorbable material. Moreover, the tubular portion 9 may be flexible, for instance, a cylindrical member may be readily deformable, such as lying in flat layers when rested against a surface. In further embodiments, the tubular portion 9 comprises a rigid or semi-rigid shape (FIG. 43C). For example, the tubular portion 9 may support the gastroesophageal reflux preventer 6 in a horseshoe, semi-circular, and/or arcuate shape. Moreover, in such instances, a support string 3 may be omitted (FIG. 43C). The tubular portion 9 may have a cross-section, such as a cylindrical, ovoid, or any other cross-section. Various cross-sectional profiles are depicted herein in FIGS. 12-20 (cross-sectional profiles 7). Moreover, the cross-sectional profile 7 of the tubular portion 9 may adapt to at least partially correspond to a shape of an organ that the tubular portion 9 is resting against.

The absorbable material may be synthetic absorbable surgical suture, such as a monofilament prepared from a copolymer of glycolide and epsilon-caprolactone. For example, the absorbable material may be poliglecaprone 25, Monocryl® available from Ethicon, and/or the like. Moreover, the absorbable material may be a synthetic absorbable surgical suture such as may be formed of a copolymer made from 90% glycolide and 10% L-lactide. For example, the absorbable material may be polyglactin 910, Vicryl® available from Ethicon, and/or the like. In various embodiments, the absorbable material may be prepared from the polyester, poly (p-dioxanone). For example, the absorbable material may be polydioxanone, PDS® II available from Ethicon, and/or the like. One may appreciate that in further embodiments, the absorbable material may be any suitable material identified by a skilled artisan.

Figure 29:
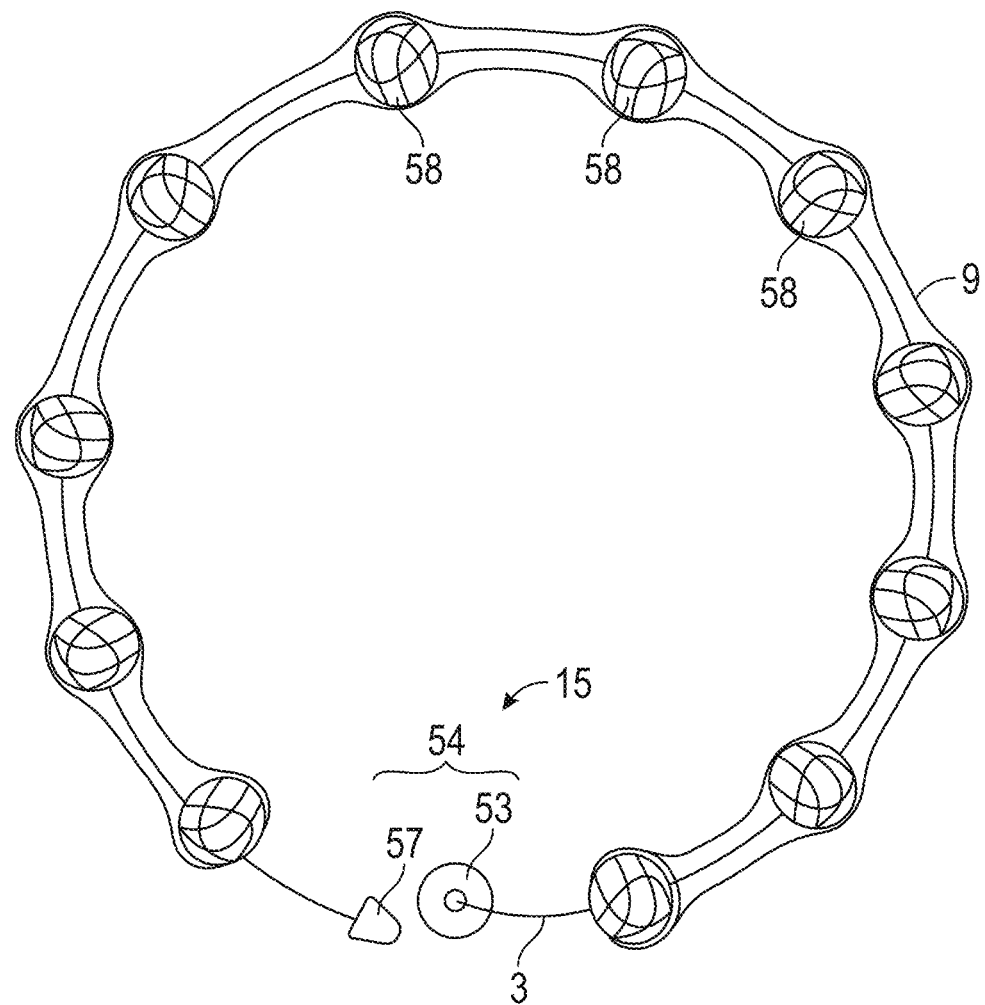
FIG. 29 illustrates an example gastroesophageal reflux treatment device with a gastroesophageal reflux preventer having a sheathed preventer including spaced nodes, and a one-way insertion closure, in accordance with various embodiments.
Figure 43A:
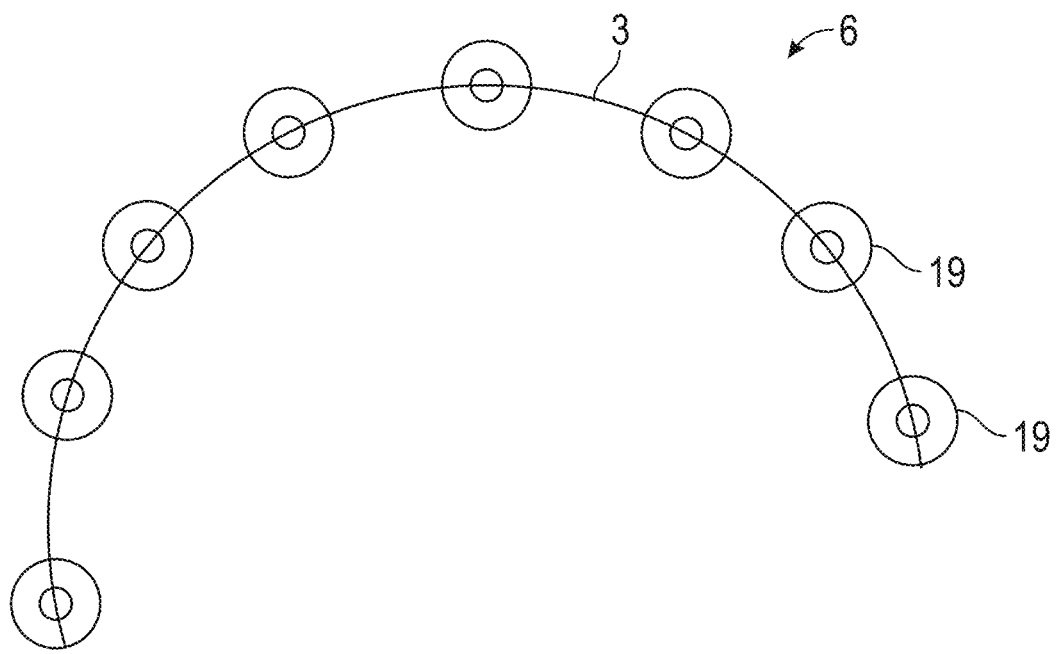
FIG. 43A illustrates an example gastroesophageal reflux treatment device that extends less than 360 degrees around a gastroesophageal sphincter of a stomach, and with a gastroesophageal reflux preventer having annular nodes, in accordance with various embodiments.
Figure 43B:
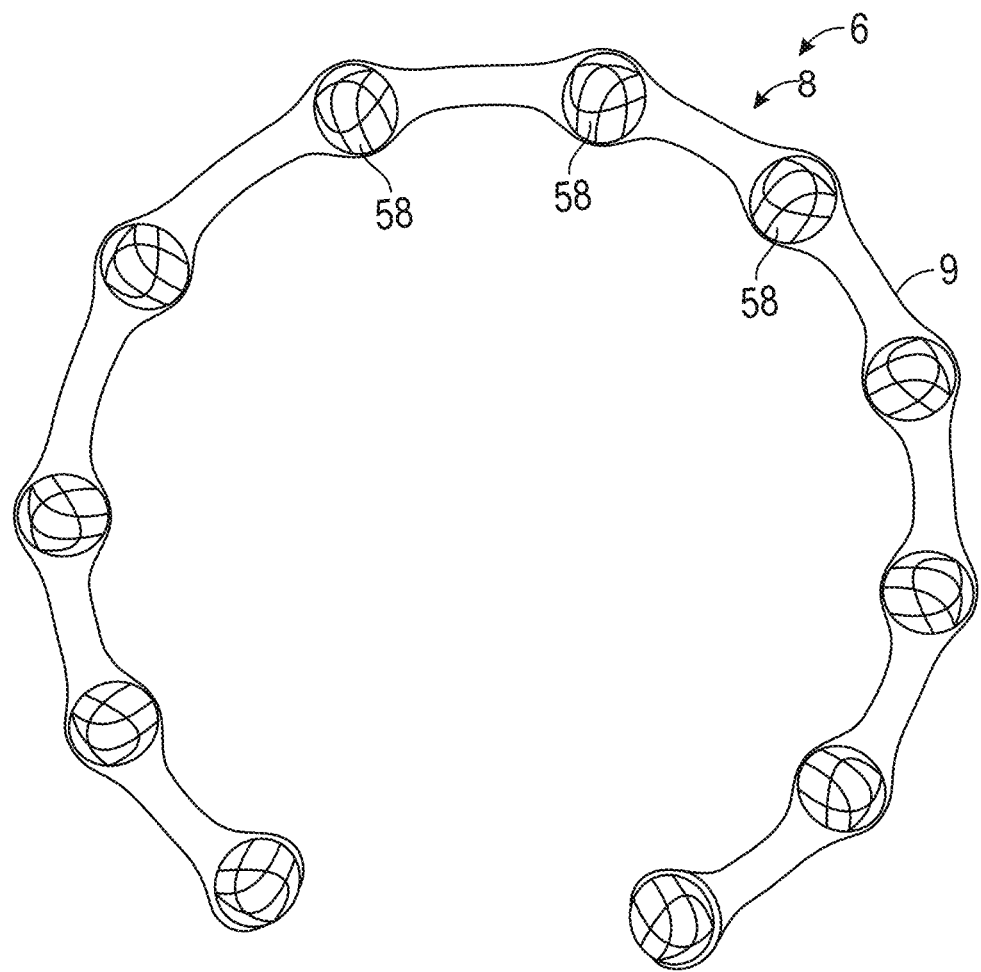
FIG. 43B illustrates an example gastroesophageal reflux treatment device that extends less than 360 degrees around a gastroesophageal sphincter of a stomach, and with a gastroesophageal reflux preventer having a sheathed preventer including spaced nodes, in accordance with various embodiments.

In various instances, the sheathed preventer 8 is filled. In further instances, the sheathed preventer 8 is hollow. A sheathed preventer 8 may be filled with a same or similar solid meshed absorbable material. The filling may be continuous, or may be intermittent. For instance, FIG. 29 depicts an elongate portion configured as sheathed preventer 8 further comprising spaced nodes 58. FIG. 43B depicts an elongate portion configured as sheathed preventer 8 further comprising spaced nodes 58, the elongate portion being rigid or semi-rigid and configured to extending only partially about a gastroesophageal sphincter, having a horseshoe, semi-circular, and/or arcuate shape. In both FIGS. 29 and 43A, spaced nodes 58 may include locally filled regions of the sheathed preventer 8. Spaced nodes 58 may have a size, shape, and spacing corresponding to a scarring profile chosen based on a given patient's degree of reduction of esophageal motility. In this manner the shape and extent of scarification may be selected to promote patient-specific desired therapeutic effects.

Figure 41:
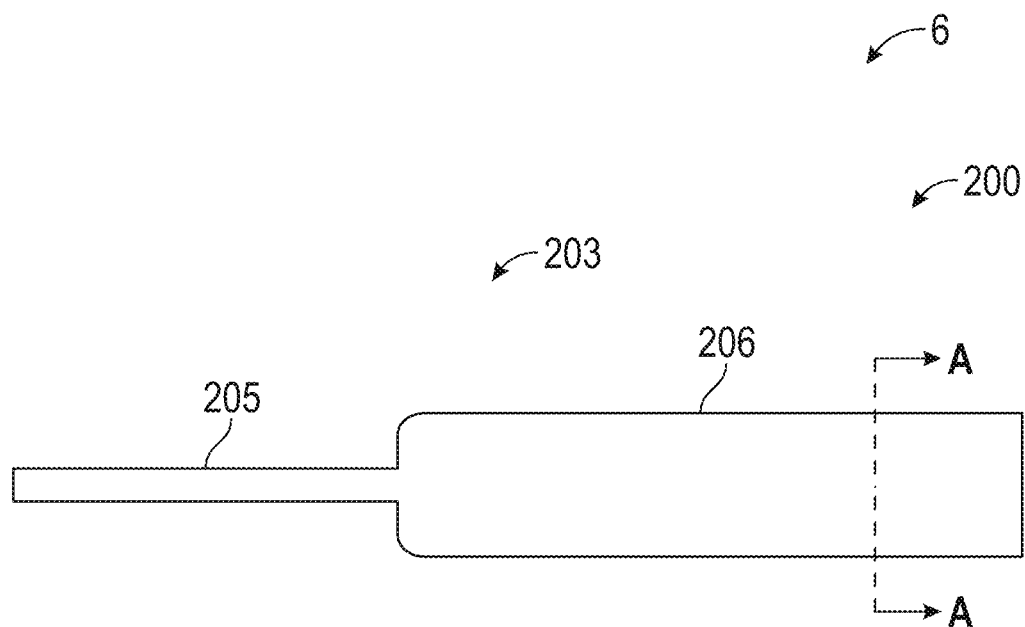
FIGS. 41-42 illustrate an example gastroesophageal reflux treatment device having a sheathed preventer with nestable ends, in accordance with various embodiments.
Figure 42:
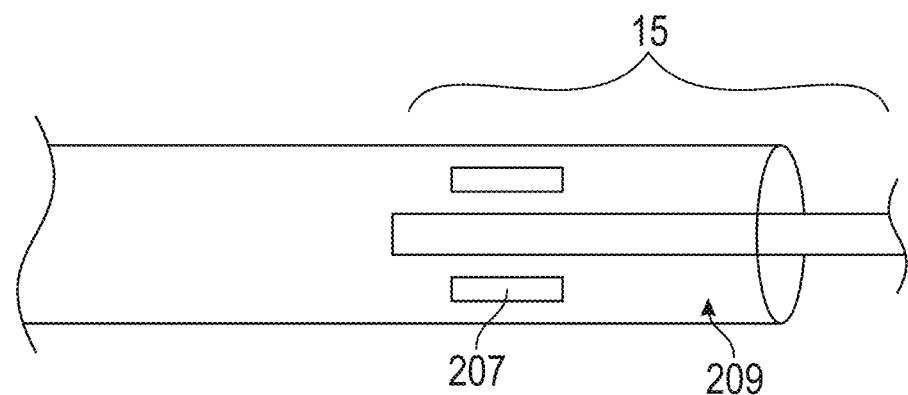
Figure 43C:
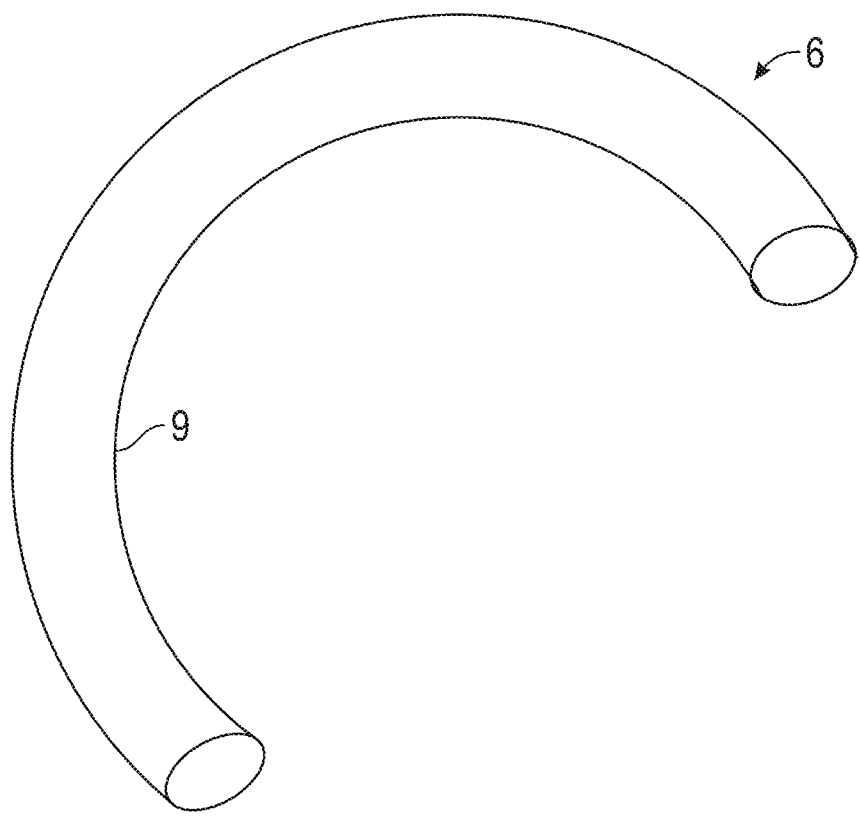
FIG. 43C illustrates an example gastroesophageal reflux treatment device that extends less than 360 degrees around a gastroesophageal sphincter of a stomach and with a gastroesophageal reflux preventer having a sheathed preventer, in accordance with various embodiments.

With specific attention to FIGS. 41-42, there is provided a gastroesophageal reflux preventer 6 comprising an elongate portion configured as a nestable sheathed preventer 200. A nestable sheathed preventer 200 may include a nestable tubular portion 203. A nestable tubular portion 203 may comprise a tube made from an absorbable material. The nestable tubular portion 203 may have a non-constant diameter, for instance a larger portion 206 may have a greater diameter than a smaller portion 205. The larger portion 206 and smaller portion 205 may be opposite ends of the nestable tubular portion 203. The smaller portion 205 may be insertable into an internal passage 209 of the larger portion 206 and retained therein by one or more suture 207. Thus, the closure mechanism 15 may comprise a suture 207 passing into the internal passage 209 to retain the smaller portion 205 therein. The nestable tubular portion 203 may have a cross-section, such as a cylindrical, ovoid, or any other cross-section. Various cross-sectional profiles are depicted herein in FIGS. 12-20 (cross-sectional profiles 7). Moreover, the cross-sectional profile 7 of the nestable tubular portion 203 may adapt to at least partially correspond to a shape of an organ that the nestable tubular portion 203 is resting against.

With reference to FIGS. 1A, 1B, 1C, 2, and 3, the gastroesophageal reflux preventer 6 may comprise an elongate portion configured as a perforated sheathed preventer 10. The perforated sheathed preventer 10 may include similar features as the sheathed preventer 8 discussed above. Moreover, the gastroesophageal reflux preventer 6 may also, in addition to the perforated sheathed preventer 10, include a support string 3 as discussed. However, the perforated sheathed preventer 10 may include a perforated tubular portion 11 which, though similar to the sheathed preventer 8, may also include one or more set of perforations defined through the perforated tubular portion 11. Sets of perforations may be spaced at different stations along the length of the perforated tubular portion 11. The perforated tubular portion 11 may be separated, such as by tearing or cutting at one or more set of perforations. In this manner, the perforated sheathed preventer 10 may be "one size fits all" meaning that the length of the perforated sheathed preventer 10 may be readily shortened to correspond to a desired geometry. For instance, the gastroesophageal reflux preventer 6 may be shortened during a surgical installation so that it corresponds to a circumference of a specific patient's esophagus, or extends only partially about a specific patient's esophagus, providing a horseshoe, semi-circular, and/or arcuate shape that rigidly or semi-rigidly retains a shape about a portion of the esophagus. Moreover, a length of the perforated tubular portion 11 may be shortened independently of a support string 3 extending therethrough. Furthermore, a support string 3 may be omitted. Thus, the scarring profile may be tailored to a patient's needs. For instance, by extending only 270 degrees or some other extent less than 360 degrees around an esophagus, the perforated tubular portion 11 may cause a scarring profile tailored to a particular patient's degree of esophageal motility.

In various instances, the perforated sheathed preventer 10 is filled. In further instances, the perforated sheathed preventer 10 is hollow. A filled perforated sheathed preventer 10 may be filled with a same or similar solid meshed absorbable material. The filling may be continuous, or may be intermittent. For instance, FIGS. 29 and 43A depict a sheathed preventer 8 further comprising spaced nodes 58. Similar spaced nodes 58 may be provided for perforated sheathed preventer 10. Spaced nodes 58 may include locally filled regions of a perforated sheathed preventer 10.

With reference to FIGS. 1A-C and 4, the gastroesophageal reflux preventer 6 may comprise an elongate portion configured as a sectioned sheath preventer 12. A sectioned sheath preventer 12 may be analogous to a sheathed preventer 8, but divided into sections. Thus, a sectioned sheath preventer 12 may include a plurality of sectioned tubular portions 13. A sectioned tubular portion 13 may comprise a tube made from an absorbable material. In various embodiments, the sectioned tubular portion 13 comprises a rounded solid meshed absorbable material. The plurality of sectioned tubular portions 13 may be curved so as to each comprise an arcuate tube. The plurality of sectioned tubular portions 13 may be rigid. In further instances, the plurality of sectioned tubular portions 13 may be flexible. Moreover, each of the plurality of sectioned tubular portions 13 may have open or closed ends, or one open end and one closed end, may be filled, may be hollow, or may be partially filled or partially hollow. Sectioned tubular portions 13 may have a size, shape, and spacing corresponding to a scarring profile chosen based on a given patient's degree of reduction of esophageal motility. In this manner the shape and extent of scarification may be selected to promote patient-specific desired therapeutic effects.

The absorbable material may be synthetic absorbable surgical suture, such as a monofilament prepared from a copolymer of glycolide and epsilon-caprolactone. For example, the absorbable material may be poliglecaprone 25, Monocryl® available from Ethicon, and/or the like. Moreover, the absorbable material may be a synthetic absorbable surgical suture such as may be formed of a copolymer made from 90% glycolide and 10% L-lactide. For example, the absorbable material may be polyglactin 910, Vicryl® available from Ethicon, and/or the like. In various embodiments, the absorbable material may be prepared from the polyester, poly (p-dioxanone). For example, the absorbable material may be polydioxanone, PDS® II available from Ethicon, and/or the like. One may appreciate that in further embodiments, the absorbable material may be any suitable material identified by a skilled artisan.

Figure 6:
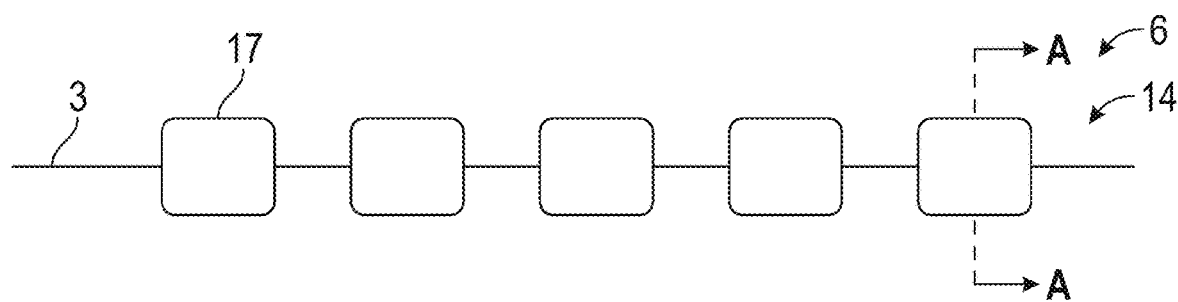
FIG. 6 illustrates an example gastroesophageal reflux treatment device having an embodiment of a linked node preventer with rounded nodes, in accordance with various embodiments.
Figure 7A:
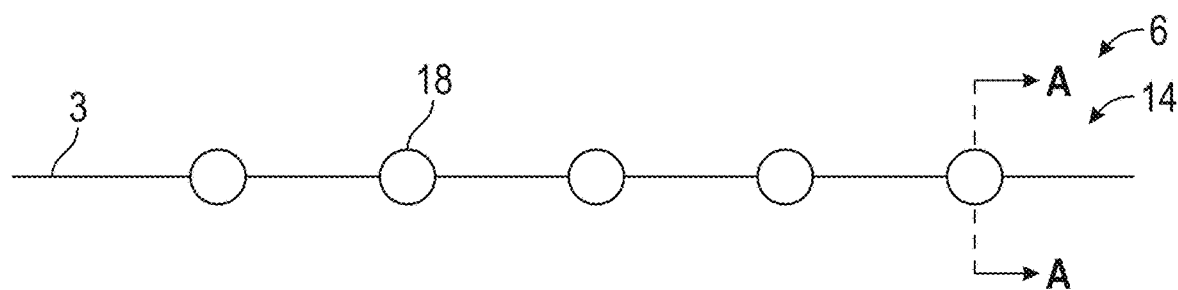
FIG. 7A illustrates an example gastroesophageal reflux treatment device having an embodiment of a linked node preventer with spherical nodes, in accordance with various embodiments.
Figure 7B:
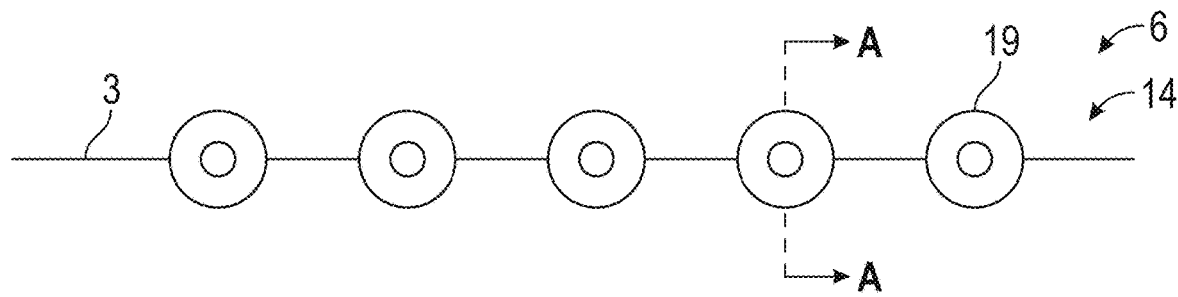
FIG. 7B illustrates an example gastroesophageal reflux treatment device having an embodiment of a linked node preventer with annular nodes, in accordance with various embodiments.
Figure 8:
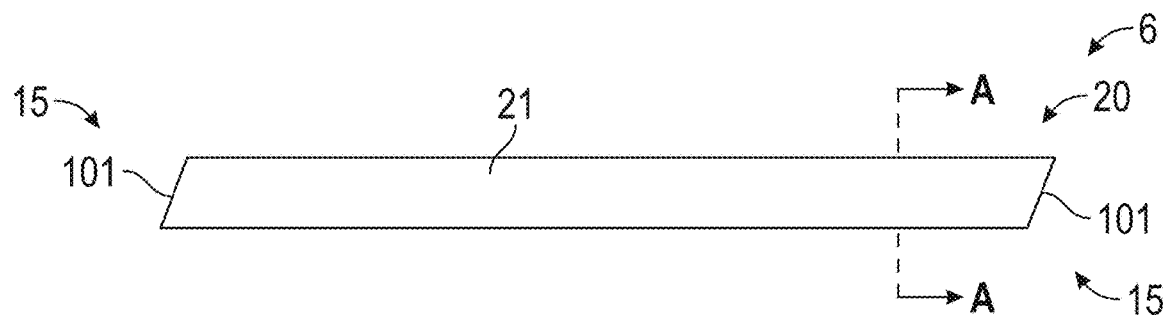
FIG. 8 illustrates an example gastroesophageal reflux treatment device having a sheet preventer, in accordance with various embodiments.
Figure 9:
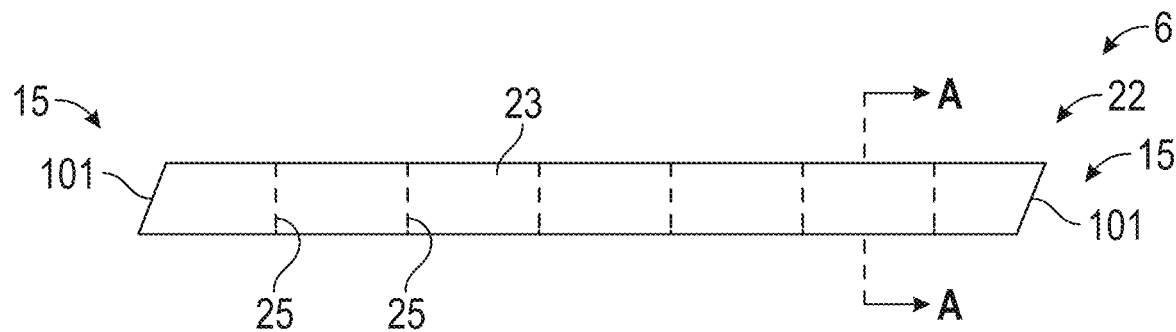
FIG. 9 illustrates an example gastroesophageal reflux treatment device having a perforated sheet preventer, in accordance with various embodiments.
Figure 10:
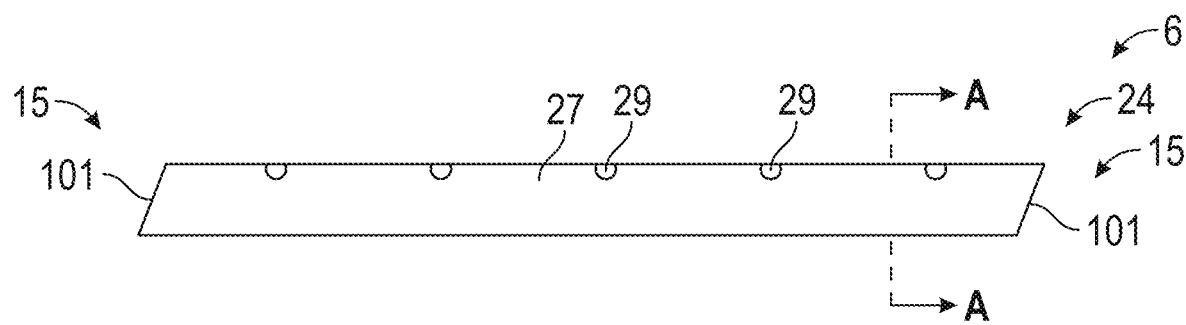
FIG. 10 illustrates an example gastroesophageal reflux treatment device having a one-side notched sheet preventer, in accordance with various embodiments.

With reference to FIGS. 1A-C and 5, the gastroesophageal reflux preventer 6 may comprise an elongate portion configured as a linked node preventer 14. A linked node preventer 14 may comprise a plurality of modules of absorbable material that are connected together by one or more string linking module to module. For example, a linked node preventer 14 may comprise one or more trapezoidal node 16. Trapezoidal node 16 may comprise a trapezoidally shaped block of absorbable material. With reference to FIG. 6, linked node preventer 14 may comprise one or more rounded node 17. A rounded node 17 may comprise a trapezoidally shaped block of absorbable material with one or more edge and/or corner that is rounded. With reference to FIG. 7A, linked node preventer 14 may comprise one or more spherical node 18. A spherical node 18 may comprise a spherically shaped block of absorbable material. With reference to FIG. 7B, linked node preventer 14 may comprise one or more annular node 19. An annular node 19 may comprise an annularly shaped block of absorbable material defining an aperture. Moreover, the various nodes described herein may, in certain embodiments, be curved so as to each comprise an arcuate node. In various instances, the nodes may be rigid, whereas in further instances, the nodes may be flexible. The curve may correspond to a curve of a surface of an organ, such as a curved surface of an esophagus.

With reference to FIGS. 1A-C and 8, in various instances, the gastroesophageal reflux preventer 6 comprises an elongate portion configured as a sheet preventer 20. A sheet preventer 20 may comprise a strip of absorbable material. The strip of absorbable material may be tie-able at the ends. For example, the strip of absorbable material may have a first end and a second end. The first end may be an opposite end of the strip from the second end. The first end and second end may be tie-able ends 101. Thus, the closure mechanism 15 may be integral with the sheet preventer 20. For shorthand ease of reference, the tie-able ends 101 may be referred to herein as portions of a support string, though no string may be provided and the sheet preventer 20 may be a one piece apparatus.

With reference to FIGS. 1A-C and 9, the gastroesophageal reflux preventer 6 may comprise an elongate portion configured as a perforated sheet preventer 22. The perforated sheet preventer 22 may include similar features as the sheet preventer 20 discussed above. However, the perforated sheet preventer 22 may include a perforated sheet portion 23 which, though similar to the sheet preventer 20, may also include one or more set of perforations 25 defined through the perforated sheet portion 23. Sets of perforations 25 may be spaced at different stations along the length of the perforated sheet portion 23. The perforated sheet portion 23 may be separated, such as by tearing or cutting, at one or more set of perforations 25. In this manner, the perforated sheet portion 23 may be "one size fits all" meaning that the length of the perforated sheet portion 23 may be readily shortened to correspond to a desired geometry. For instance, the gastroesophageal reflux preventer 6 may be shortened during a surgical installation so that it corresponds to a circumference of a specific patient's esophagus, or a desired scarring profile depending on a patient's physiology, esophageal motility, treatment objectives, etc.

With reference to FIGS. 1A-C and 10, the gastroesophageal reflux preventer 6 may comprise an elongate portion configured as a one-side notched sheet preventer 24. The one-side notched sheet preventer 24 may include similar features as the sheet preventer 20 discussed above. However, the one-side notched sheet preventer 24 may include a notched sheet portion 27 which, though similar to the sheet preventer 20, may also include first edge notches 29. First edge notches 29 are spaced apart notches along a first edge. First edge notches 29 may be spaced at different stations along the length of the notched sheet portion 27. The notched sheet portion 27 may be separated, such as by tearing or cutting, at one or more first edge notches 29. In this manner, the notched sheet portion 27 may be "one size fits all" meaning that the length of the notched sheet portion 27 may be readily shortened to correspond to a desired geometry. For instance, the gastroesophageal reflux preventer 6 may be shortened during a surgical installation so that it corresponds to a circumference of a specific patient's esophagus, or a desired scarring profile depending on a patient's physiology, esophageal motility, treatment objectives, etc.

With reference to FIGS. 1A-C and 11, the gastroesophageal reflux preventer 6 may comprise an elongate portion configured as a dual-side notched sheet preventer 26. The dual-side notched sheet preventer 26 may include similar features as the sheet preventer 20 discussed above. However, the dual-side notched sheet preventer 26 may include a notched sheet portion 27 which, though similar to the sheet preventer 20, may also include first edge notches 29 and also includes second edge notches 31. First edge notches 29 are spaced apart notches along a first edge of the notched sheet portion 27. First edge notches 29 may be spaced at different stations along the length of the notched sheet portion 27.

Second edge notches 31 are spaced apart notches along a second edge of the notched sheet portion 27 opposite the first edge notches 29. Second edge notches 31 may be spaced at different stations along the length of the notched sheet portion 27. In various embodiments, the first edge notches 29 and the second edge notches 31 are spaced apart along their respective first and second edges of the notched sheet portion 27 such that each first edge notch 29 corresponds to a second edge notch 31 at a same station along the length of the notched sheet portion 27. Moreover, the notched sheet portion 27 may be separated, such as by tearing or cutting, at one or more first edge notches 29 and at one of the one or more second edge notches 31. For instance, a tear or cut may be started at a first edge notch 29 and end at a second edge notch 31. Alternatively, a tear or cut may be started at a second edge notch 31 and may end at a first edge notch 29. In this manner, the notched sheet portion 27 may be "one size fits all" meaning that the length of the notched sheet portion 27 may be readily shortened to correspond to a desired geometry. For instance, the gastroesophageal reflux preventer 6 may be shortened during a surgical installation so that it corresponds to a circumference of a specific patient's esophagus, or a desired scarring profile depending on a patient's physiology, esophageal motility, treatment objectives, etc.

Having introduced various embodiments of gastroesophageal reflux preventer 6, attention is shifted to FIGS. 1A-C and 12-20 for a discussion of various cross-sectional profiles 7 that several of the different gastroesophageal reflux preventers 6 discussed herein may include. For example, section lines A-A are depicted in FIGS. 12-20 corresponding to a section view A-A. The section view A-A corresponds to a cross-sectional profile 7 of the various different gastroesophageal reflux preventers 6. Thus, with reference to FIGS. 12-20, one may appreciate that in different embodiments, different cross-sectional profiles 7 may be adopted.

For example, referring to all FIGS. 1-43C, the cross-sectional profiles 7 discussed herein may comprise a cross-sectional shape of an elongate portion configured as a tubular portion 9 of a sheathed preventer 8. The cross-sectional profiles 7 discussed herein may comprise a cross-sectional shape of an elongate portion configured as a perforated tubular portion 11 of a perforated sheathed preventer 10. The cross-sectional profiles 7 discussed herein may comprise a cross-sectional shape of an elongate portion configured as a sectioned tubular portion 13 of a sectioned sheath preventer 12 (and different sectioned tubular portions 13 of a same sectioned sheath preventer 12 may have different cross-sectional profiles 7). The cross-sectional profiles 7 discussed herein may comprise a cross-sectional shape of a node of an elongate portion configured as linked node preventer 14, including a trapezoidal node 16, a rounded node 17, a spherical node 18, and/or an annular node 19. Different nodes of a linked node preventer 14 may have different cross-sectional profiles 7. The cross-sectional profiles 7 discussed herein may comprise a cross-sectional shape of an elongate portion configured as a sheet portion 21 of a sheet preventer 20. The cross-sectional profiles 7 discussed herein may comprise a cross-sectional shape of an elongate portion configured as a perforated sheet portion 23 of a perforated sheet preventer 22. The cross-sectional profiles 7 discussed herein may comprise a cross-sectional shape of an elongate portion configured as a notched sheet portion 27 of a one-side notched sheet preventer 24. The cross-sectional profiles 7 discussed herein may comprise an elongate portion configured as a cross-sectional shape of a notched sheet portion 27 of a dual-side notched sheet preventer 26. In addition, different portions or aspects of a gastroesophageal reflux preventer 6 may have different cross-sectional profiles 7, for instance, the cross-sectional profile 7 of a gastroesophageal reflux preventer 6 may change from location to location. The cross-sectional profile 7 may correspond to a desired scarring profile. Moreover, and with reference to FIGS. 1-43C, in any embodiments discussed herein, various further embodiments may contemplate the omission of the support string 3. Furthermore, in any embodiments discussed herein, various further embodiments may contemplate the omission of the closure mechanism 15. In any embodiments discussed herein, various further embodiments may contemplate the omission of both the support string 3 and the closure mechanism 15. Further additionally, various embodiments may contemplate the omission of one or both of the support string 3 and the closure mechanism 15 and may be at least partially rigid and/or semi-rigid, as well as may only partially encircle a body part associated with a sphincter. Furthermore, a support string 3 may be present for emplacement and may be removable. In yet further instances, one or more portion of the gastroesophageal reflux preventer 6, including, for example, the elongate portion, the support string, and/or the closure mechanism may not be absorbable. Still furthermore, an opening may be defined in at least a part of the gastroesophageal reflux preventer 6, the opening comprising a suture portion for the insertion of a suture to affix the gastroesophageal reflux preventer 6 in position relative to a body tissue. The opening may be a aperture such as through an annular node 19.

More specifically, with reference to FIGS. 1A-C and 12, a cross-sectional profile 7 of a gastroesophageal reflux preventer 6 may comprise a trapezoidal cross-section 28. A trapezoidal cross-section 28 may comprise a rectangle. In further instances, a trapezoidal cross-section 28 may comprise a square. A trapezoidal cross-section 28 may comprise a parallelogram. A trapezoidal cross-section 28 may comprise a rhombus. A trapezoidal cross-section 28 may comprise a trapezoid or quadrilateral or any four sided shape as desired. Moreover, the corners of the trapezoidal cross-section 28 may include acute angles, obtuse angles, right angles, curves, chamfers, and/or other features as desired.

More specifically, with reference to FIGS. 1A-C and 13, a cross-sectional profile 7 of a gastroesophageal reflux preventer 6 may comprise a concave cross-section 30. A concave cross-section 30 may comprise one or more arc. The one or more arc may be positioned to provide at least one surface of the gastroesophageal reflux preventer 6 that is concave. When rested against an organ, such as a stomach and/or esophagus, the concavity faces the organ, such that the concavity corresponds to a gap between the organ and at least a portion of the concave surface of the gastroesophageal reflux preventer 6. The gap is disposed between two regions of lesser gap and/or greater contact between the concave surface of the gastroesophageal reflux preventer 6 and the organ.

Furthermore, now with reference to FIGS. 1A-C and 14, a cross-sectional profile 7 of a gastroesophageal reflux preventer 6 may comprise a convex cross-section 32. A convex cross-section 32 may comprise one or more arc. The one or more arc may be positioned to provide at least one surface of the gastroesophageal reflux preventer 6 that is convex. When rested against an organ, such as a stomach and/or esophagus, the convexity faces the organ. In various embodiments, the convexity corresponds to a gap between the organ and at least a portion of the convex surface of the gastroesophageal reflux preventer 6. For example, the gap may be disposed on opposite sides an intermediate region of lesser gap and/or greater contact between the convex surface of the gastroesophageal reflux preventer 6 and the organ.

Moreover, in various embodiments the convexity corresponds to a profile of an organ. For example, an esophagus and a stomach may connect together. Body tissue proximate to the junction may have a curve, such as so that the esophagus wall transitions along a curvature to a stomach wall. The convexity may correspond to the shape of a union of an esophagus and a stomach. The convexity may correspond to a profile of an organ. In this manner, the surface of the convexity may rest against a corresponding surface of a body organ. Thus, a convex cross-section 32 may be said to nest against a curve of a body organ.

Directing attention now to FIGS. 1A-C and 15, a cross-sectional profile 7 of a gastroesophageal reflux preventer 6 may comprise a flat cross-section 34. For example, a flat cross-section 34 may include at least one planar surface. In various embodiments, one or more edge of the planar surface is rounded, such as to ameliorate force concentrations between an edge of the planar surface and body organ.

Shifting focus now to FIGS. 1A-C and 16, a cross-sectional profile 7 of a gastroesophageal reflux preventer 6 may comprise an oval cross-section 36. The oval cross-section 36 may comprise a continuous arc of varying radius. The oval cross-section 36 may have a longer diameter and a shorter diameter. The longer diameter may facilitate improved contact area between a body organ and the gastroesophageal reflux preventer 6 and the shorter diameter may facilitate correspondence of a profile of a portion of the oval cross-section 36 to a corresponding surface of a body organ, such as to be said to nest against a curve of a body organ. In this manner, the shorter diameter may correspond to a shape of a union of an esophagus and a stomach, while the longer diameter may correspond to an improved contact area between a stomach and the gastroesophageal reflux preventer 6.

With reference to FIGS. 1A-C and 17, a cross-sectional profile 7 of a gastroesophageal reflux preventer 6 may comprise a round cross-section 38. For example, the round cross-section 38 may comprise a continuous arc of constant radius. The round cross-section 38 may facilitate improved contact area between a union of an esophagus and a stomach, for instance, the round cross-section 38 may comprise a diameter selected to facilitate nesting of the round cross-section 38 against a curve of a body organ, such as a shape of a union of an esophagus and a stomach.

A gastroesophageal reflux preventer 6 may include multiple portions of material that are collected together such as strands collected into a rope, strands collected into a braid, and/or similar. For instance, a gastroesophageal reflux preventer 6 may have a cross-sectional profile 7 as shown in FIG. 18. With reference to FIG. 1A-C and 18, a cross-sectional profile 7 of a gastroesophageal reflux preventer 6 may comprise multiple cross-sections of multiple portions of material that are collected together to form the gastroesophageal reflux preventer 6. For instance, a cross-sectional profile 7 of a gastroesophageal reflux preventer 6 may comprise a collection of round strands to form a larger cord-like strand, for instance, a collection of round cross-sections assembled to provide a stranded cross-section 40. While the stranded cross-section 40 shows a collection of strands that itself approximates the shape of the constituent strands, in further instances, the cross-section of each strand and the collection of the strands may be dissimilar. For instance, strands with a round cross-section (FIG. 17) may be assembled into a stranded cross-section 40 that approximates a trapezoidal cross-section 28 (FIG. 12).

With reference to FIGS. 1A-C and 19, a cross-sectional profile 7 of a gastroesophageal reflux preventer 6 may comprise a t-shape cross-section 42. For example, the cross-section may include at least two arms joining at an angle. In various instances, t-shape cross-section 42 comprises two arms bisecting at a right angle. Stated differently, t-shape cross-section 42 may comprise four arms extending outwardly from a junction wherein each arm is at a right angle to at least two other such arms and parallel to at least one other such arm. One may appreciate that the different arms may be of different lengths, and may be at angles other than right angles with respect to each other, for instance, a t-shape cross-section 42 may resemble an X-shape, in further embodiments.

In further instances, a cross-sectional profile 7 of a gastroesophageal reflux preventer 6 may comprise an L-shape cross-section 44, such as is depicted in FIG. 20. With reference to FIGS. 1A-C and 20, an L-shape cross-section 44 may comprise two arms joining at an angle. In various instances, the L-shape cross-section 44 may comprise two arms extending outwardly from a junction where the two arms join at a right angle. One may appreciate that the arms may be of different lengths, and may be at angles other than a right angle with respect to each other, for instance, L-shape cross-section 44 may resemble a V-shape, in further embodiments.

Having introduced a variety of embodiments of gastroesophageal reflux preventers 6 comprising a variety of configurations, attention is now directed to the previously mentioned closure mechanism 15 (FIG. 1). Various different gastroesophageal reflux preventers 6 may include various closure mechanisms 15 in order to retain the gastroesophageal reflux preventer 6 to an organ, such as an esophagus and/or stomach. In various instances, the closure mechanism 15 does not connect the gastroesophageal reflux preventer 6 in direct fixation to the organ, but captures the gastroesophageal reflux preventer 6 in loose proximity to the organ. For instance, opposite ends of an aspect of the gastroesophageal reflux preventer 6 may be tied about an esophagus, retaining the gastroesophageal reflux preventer 6 in proximity to the esophagus but not requiring suturing directly to the esophagus. In further instances, the closure mechanism 15 is omitted (FIG. 1C) and the gastroesophageal reflux preventer 6 is held in position by rigidity and/or semi-rigidity and/or suturing. Moreover, in various such embodiments, the ends of the gastroesophageal reflux preventer 6 are not connected together.

With reference to FIGS. 1A-B and 21-25, a few example embodiments of a closure mechanism 15 are provided. For example, with reference to FIGS. 1A-B and 21, a closure mechanism 15 may comprise a knot 5. A knot 5 may be formed in a support string 3 as mentioned herein, or a knot 5 may be formed in opposite ends of a portion such as a tubular portion 9, perforated tubular portion 11, sectioned tubular portion 13, and or the previously mentioned tie-able ends 101 (see FIGS. 1A-19) that have been discussed.

A knot 5 may comprise a bow knot closure 46. For instance, as shown in FIG. 21, a bow knot closure 46 may be tied such that a bow knot is formed, such as to facilitate easy release of the knot 5 for later removal and/or adjustment. With reference to FIG. 22, a knot 5 may comprise a square knot closure 48, such that a square knot is tied.

Figure 24:
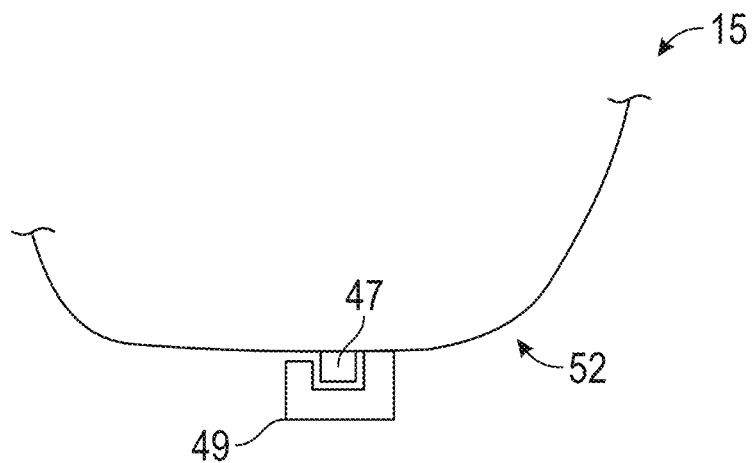
FIG. 24 illustrates an example gastroesophageal reflux treatment device with a closure mechanism corresponding to an outward clasp closure, in accordance with various embodiments.

Turning attention to FIG. 23, a closure mechanism 15 may comprise an inward clasp closure 50. For instance, a pin 47 may be provided to be received into a slot 49 attached to the pin 47 such as by deformation and snap fitting, or by friction fitting, and/or the like. The combination of the pin 47 and slot 49 may be disposed inwardly of the closed outer boundary (e.g., inwardly of the outward edge of the elongate portion) of the gastroesophageal reflux preventer 6 when the pin 47 and slot 49 are connected. In further instances, and as shown in FIG. 24, a closure mechanism 15 may comprise an outward clasp closure 52. An outward clasp closure 52 may include a similar pin 47 and slot 49 aspect, however, the combination of the pin 47 and slot 49 may be disposed outwardly of the closed inner boundary (e.g., outward of the inner edge of the elongate portion) of the gastroesophageal reflux preventer 6 when the pin 47 and slot 49 are connected.

Figure 25:
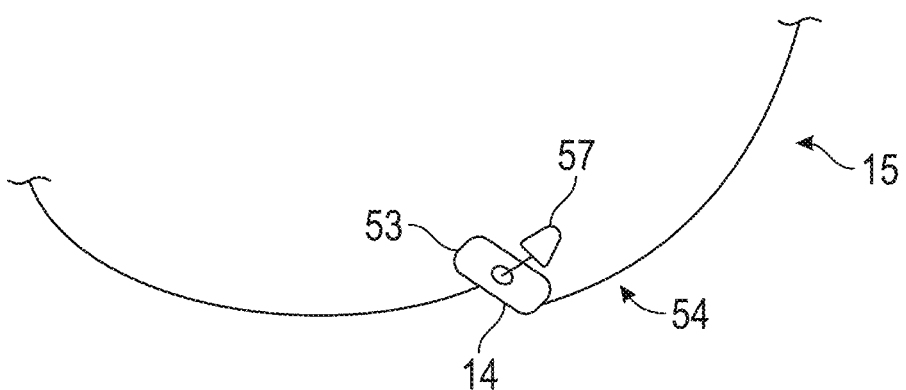
FIG. 25 illustrates an example gastroesophageal reflux treatment device with a closure mechanism corresponding to a one-way insertion closure, in accordance with various embodiments.

Finally, and with reference to FIGS. 1A-B and 25, a one-way insertion closure 54 may be provided. A closure mechanism 15 comprising a one-way insertion closure 54 may provide for easy closure by medical personnel during installation of the gastroesophageal reflux preventer 6, but may resist opening following installation, so as to facilitate reliable emplacement without migration in a living body.

For example, a gastroesophageal reflux preventer 6 may include a support string 3 mentioned elsewhere herein. The support string 3 may have two ends extending oppositely from the gastroesophageal reflux preventer 6. The one-way insertion closure 54 may include a thickened tab 57 attached proximate to a first end of the support string 3, and a slotted receiver 53 attached proximate to a second end of the support string 3 opposite the first end.

A thickened tab 57 may comprise a portion of a support string 3, or a separate member attached to the end of the support string 3, that is thicker than the support string 3. In various embodiments, the thickened tab 57 is only partially thicker than the support string 3. For example, the thickened tab 57 may be tapered such that a tip of the thickened tab 57 is thinner than a root of the thickened tab 57 where the root is the end of the thickened tab 57 closest to the support string 3 and the tip is the end of the thickened tab 57 cantilevered distally farthest from the support string 3. In various embodiments, the thickened tab 57 may be cone-shaped. Thus the thickened tab 57 may be self-aligning with a slotted receiver 53, so that the thin tip readily inserts into a portion of a slotted receiver 53, and as the thickened tab 57 is inserted further into the slotted receiver 53, the thickened tab 57 progressively fills the slotted receiver 53. The thickened tab 57 may be sized to progressively become larger than a corresponding aperture in the slotted receiver 53, such that the thickened tab 57 is compressed during insertion into an aperture of the slotted receiver 53, and following passage through the aperture of the slotted receiver 53, uncompresses to become larger than the aperture, such that the thickened tab 57 is restricted from passing oppositely through the aperture and disconnecting therefrom.

Figure 11:
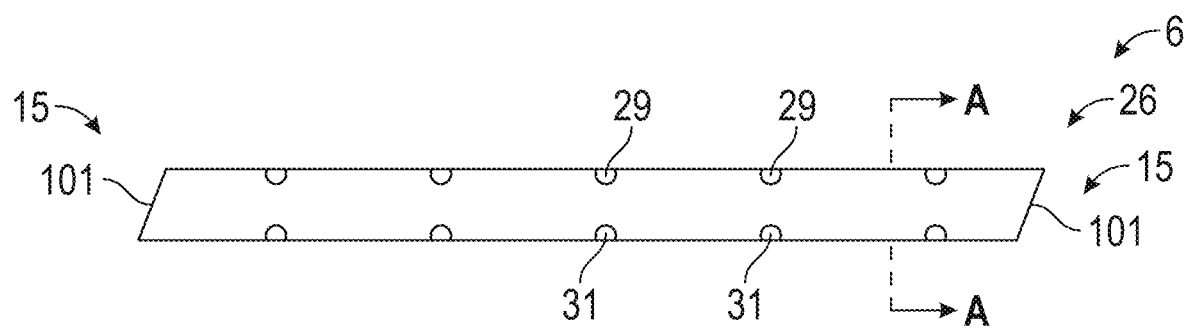
FIG. 11 illustrates an example gastroesophageal reflux treatment device having a dual-side notched sheet preventer, in accordance with various embodiments.

The slotted receiver 53 may comprise a portion of a support string 3, or a separate member attached to an end of the support string 3. The slotted receiver 53 may be a spaced node 58 (FIG. 29), or a sectioned tubular portion 13 of a sectioned sheath preventer 12 (FIG. 4), or a node of a linked node preventer 14 (FIGS. 5-7B), or may be an aperture of a sheet portion 21 of a sheet preventer 20 (FIG. 8), or may be an aperture of a perforated sheet portion 23 of a perforated sheet preventer 22 (FIG. 9) or may be an aperture of a notched sheet portion 27 of a one-side notched sheet preventer 24 (FIG. 10) or of a dual-side notched sheet preventer 26 (FIG. 11). The slotted receiver 53 may comprise an annular node 19 (FIGS. 7B, 26) of a linked node preventer 14 (FIGS. 7B, 26) defining an aperture through an annulus. The thickened tab 57 may be insertable through the annular node 19. Annular nodes 19 may be positioned along the support string so that a variety of options for insertion of the thickened tab 57 are available. In this manner, the length of the gastroesophageal reflux preventer 6 may be tailored to a specific patient's needs, and then excess support string 3 and/or excess annular nodes 19 may be cut free and removed.

Figure 26:
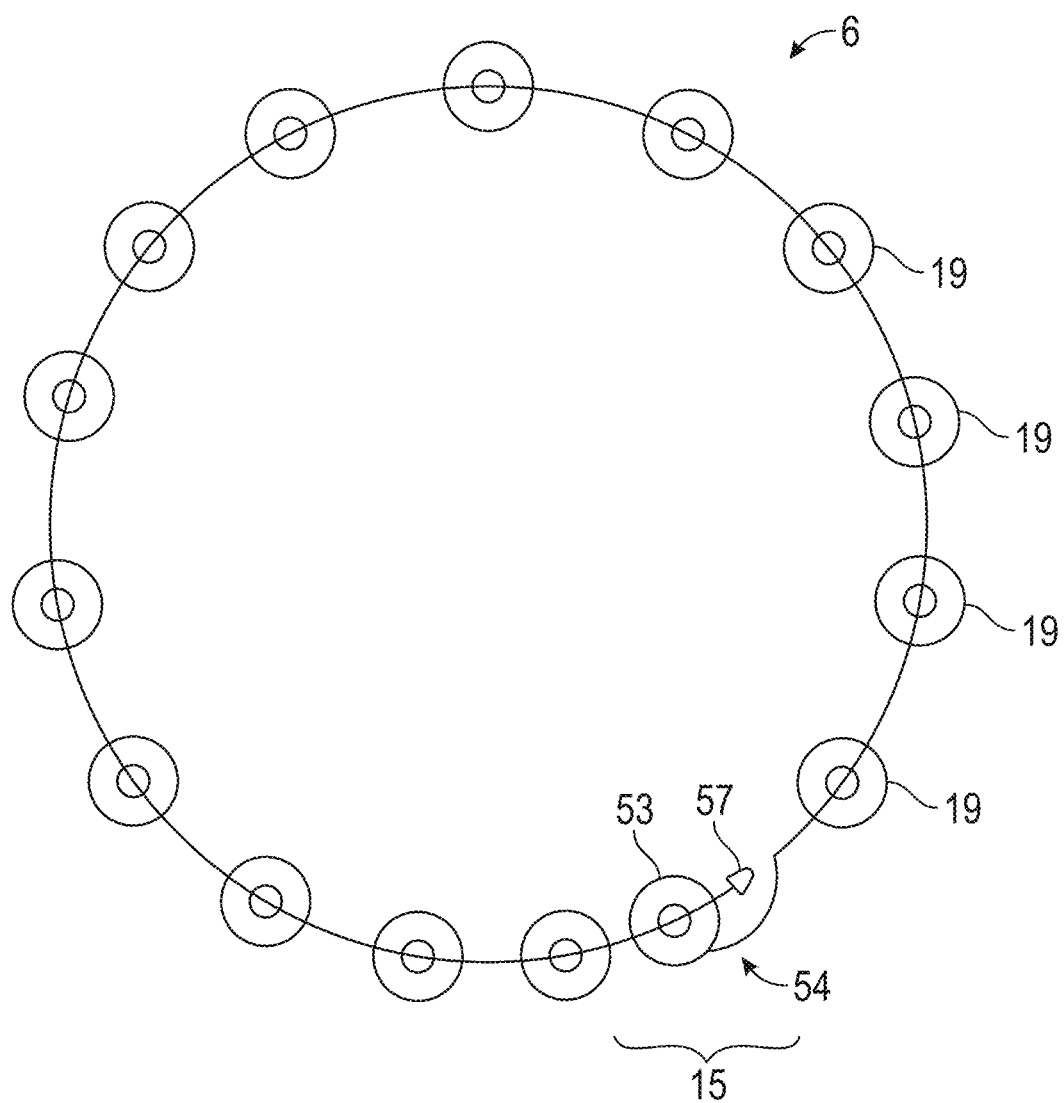
FIG. 26 illustrates an example gastroesophageal reflux treatment device with a gastroesophageal reflux preventer having annular nodes, in accordance with various embodiments.

Having introduced various configurations of gastroesophageal reflux preventers 6, various examples of different embodiments that combine subsets of features will now be discussed. Turning first to FIGS. 26 and 43A, a gastroesophageal reflux preventer 6 may include a linked node preventer 14 with annular nodes 19 spaced apart along a support string 3. The support string 3 has two ends that may be tied about an esophagus. The support string 3 may extend only as far as the endmost linked node preventers 14 and may support a rigid or semi-rigid gastroesophageal reflux preventer 6 in non-enclosing relation partially encircling a gastroesophageal sphincter, not having ends extending for connection together (FIG. 43A). Alternatively, the support string 3 may have a closure mechanism 15 comprising a one-way insertion closure 54 with a thickened tab 57 at one end of the support string 3 and a slotted receiver 53 provided by an annular node 19 at the other end of the support string 3. In various embodiments, medical personnel installing the gastroesophageal reflux preventer 6 may select from among multiple different annular nodes 19, so as to size the gastroesophageal reflux preventer 6 to a specific patient's specific anatomy. The excess annular nodes 19 and excess support string 3 remaining after insertion of a thickened tab 57 into a slotted receiver 53 may be cut free and removed from a patient's body.

Figure 27:
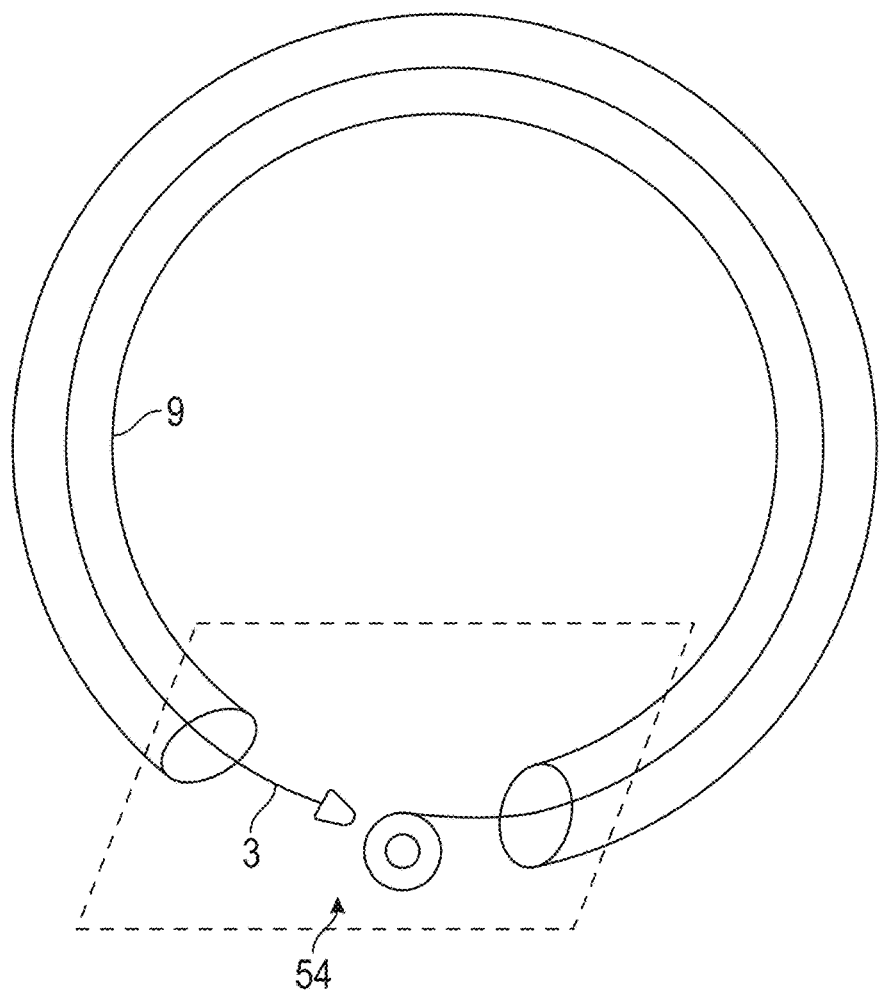
FIGS. 27-28 illustrates an example gastroesophageal reflux treatment device with a gastroesophageal reflux preventer having a sheathed preventer and a one-way insertion closure, in accordance with various embodiments.
Figure 28:
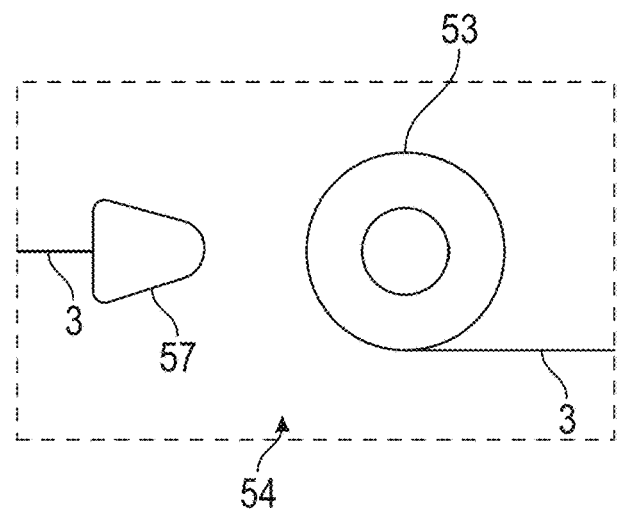

Turning now to FIGS. 27, 28, and 43C, another embodiment includes a sheathed preventer 8 in combination with a closure mechanism 15 (or as in FIG. 43C, omitting the closure mechanism 15 and including rigidity and/or semi-rigidity) comprising a one-way insertion closure 54. A tubular portion 9 of a sheathed preventer 8 may have a support string 3 extending through it, and/or having separate support string 3 portions attached to opposite ends thereof, or omitting the support string 3 and having rigidity and/or semi-rigidity. A one-way insertion closure 54 may include a thickened tab 57 from one end of the support string 3 and a slotted receiver 53 from another end of the support string 3. In various instances, the slotted receiver 53 may be an annulus defining an aperture to receive the thickened tab 57, such as an annular node 19.

Further embodiments are depicted in FIGS. 29 and 43B. For instance, a sheathed preventer 8 has been discussed elsewhere herein, however, in various embodiments a sheathed preventer 8 includes spaced nodes 58 included as a part of a tubular portion 9 having a support string 3 extending through it, and/or having separate support string 3 portions attached to opposite ends thereof, and/or having no support string or a support string that does not extend beyond the endmost spaced nodes 58 (FIG. 43B). The sheathed preventer 8 may be combined with a closure mechanism 15 comprising a one-way insertion closure 54.

The sheathed preventer 8 may omit a closure mechanism 15, being rigid or semi-rigid and extending at least partially about a gastroesophageal sphincter, and retained in position by the rigidity and/or semi-rigidity, and/or sutures. A one-way insertion closure 54 may include a thickened tab 57 from one end of the support string 3 and a slotted receiver 53 from another end of the support string 3. In various instances, the slotted receiver 53 may be an annulus defining an aperture to receive the thickened tab 57, such as an annular node 19.

Figure 30:
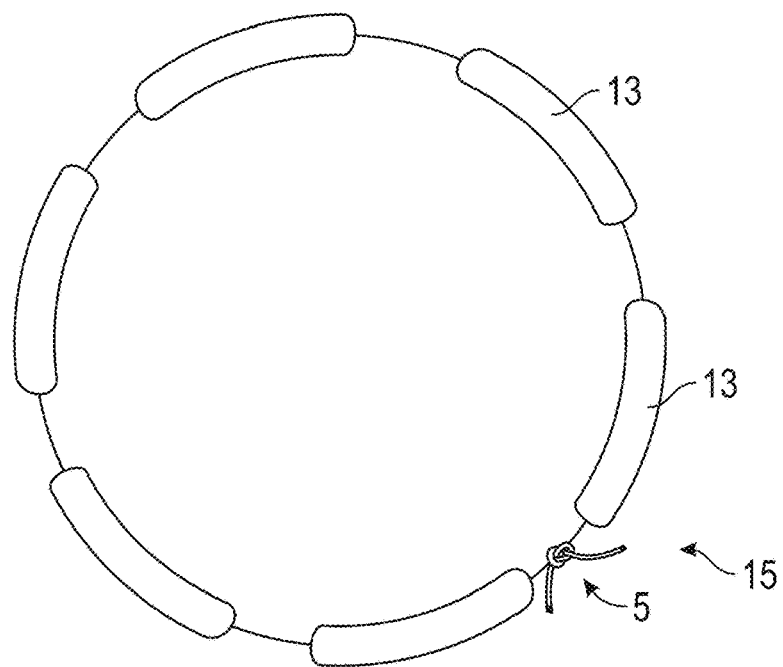
FIG. 30 illustrates an example gastroesophageal reflux treatment device with a gastroesophageal reflux preventer having a sectioned sheathed preventer, in accordance with various embodiments.

Yet a further embodiment is depicted in FIG. 30 wherein a sectioned sheath preventer 12 is provided in connection with support string 3 and a closure mechanism 15 comprising a knot 5.

Figure 31:
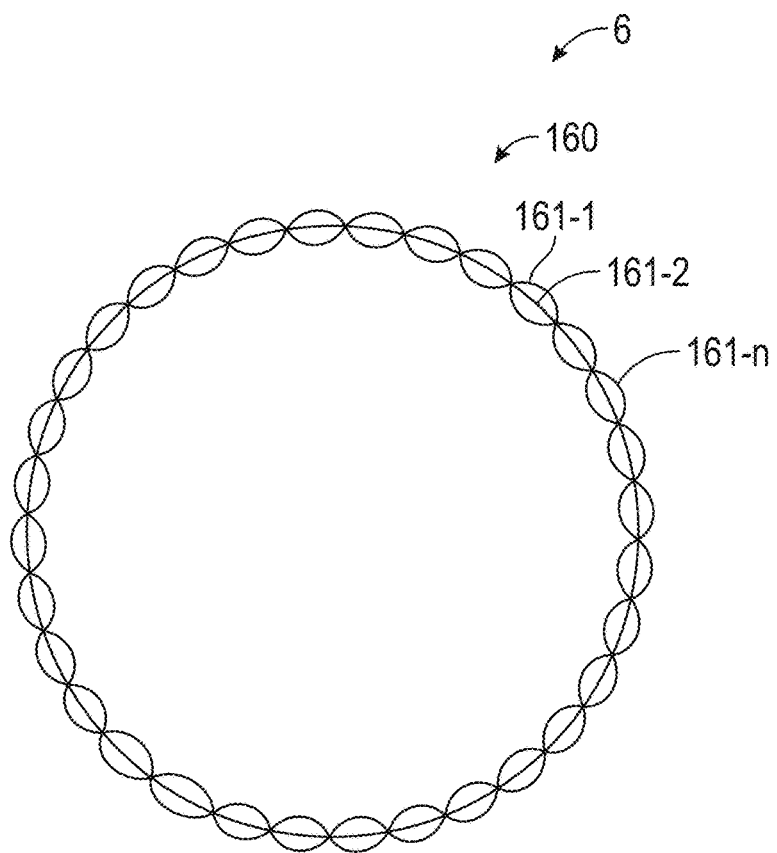
FIG. 31 illustrates an example gastroesophageal reflux treatment device with a gastroesophageal reflux preventer having a braided multi-strand preventer, in accordance with various embodiments.
Figure 32:
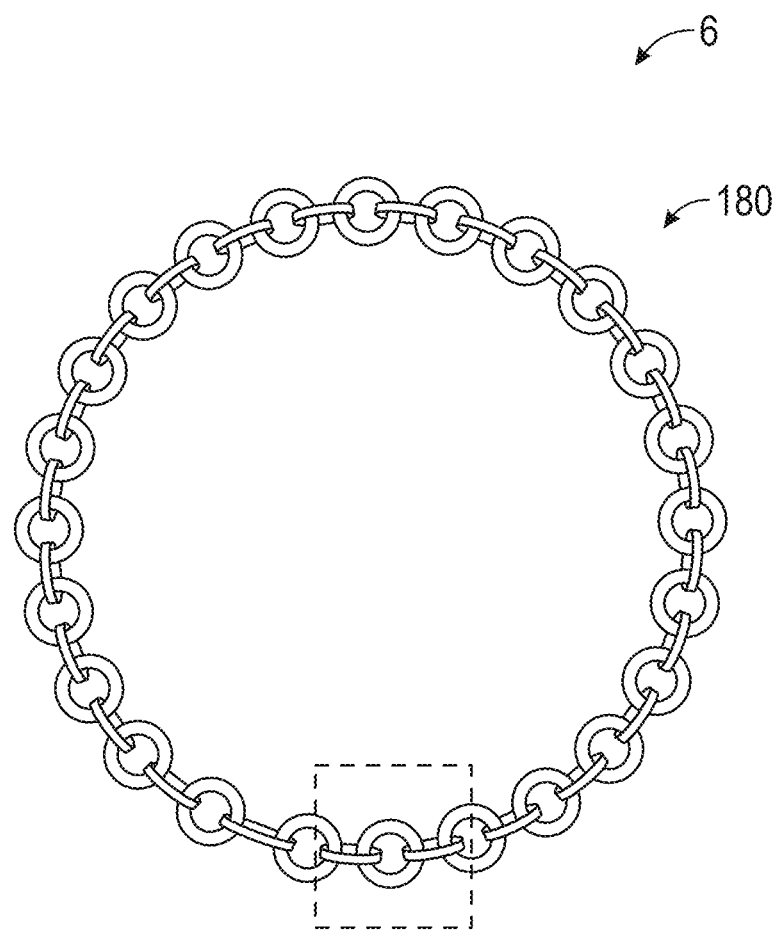
FIG. 32 illustrates an example gastroesophageal reflux treatment device with a gastroesophageal reflux preventer having a chain-link multi-strand preventer, in accordance with various embodiments.
Figure 33:
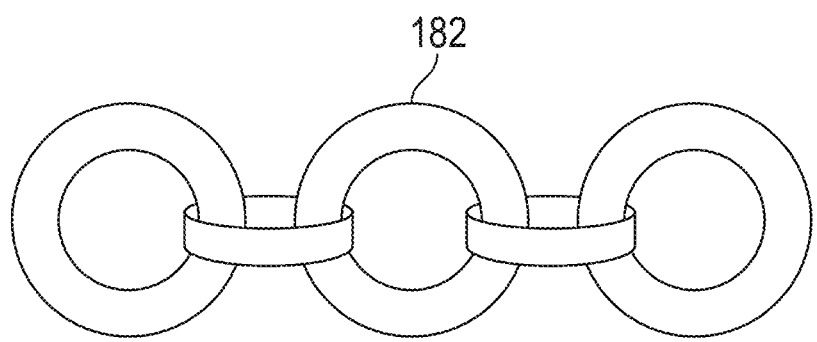
FIG. 33 illustrates a round link of a chain-link multi-strand preventer, in accordance with various embodiments.
Figure 34:
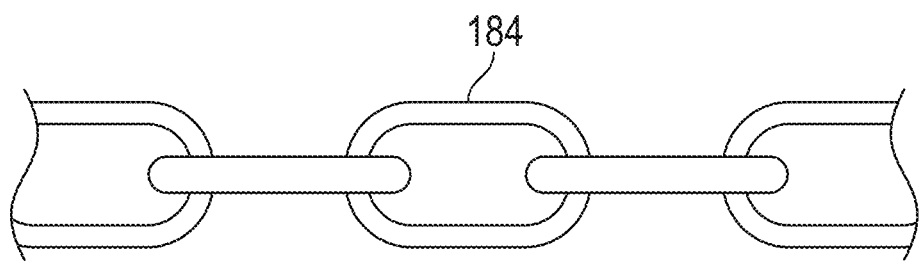
FIG. 34 illustrates a stretched link of a chain-link multi-strand preventer, in accordance with various embodiments.
Figure 35:
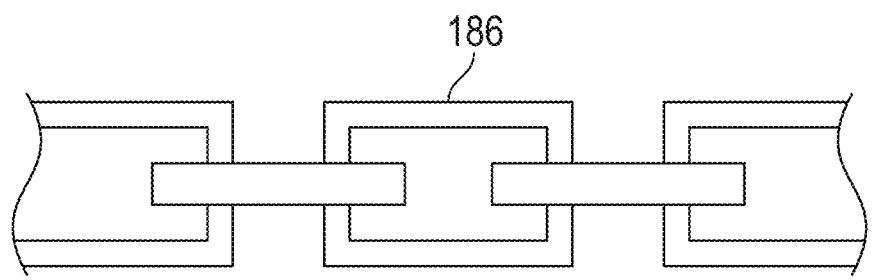
FIG. 35 illustrates a trapezoidal link of a chain-link multi-strand preventer, in accordance with various embodiments.
Figure 36:
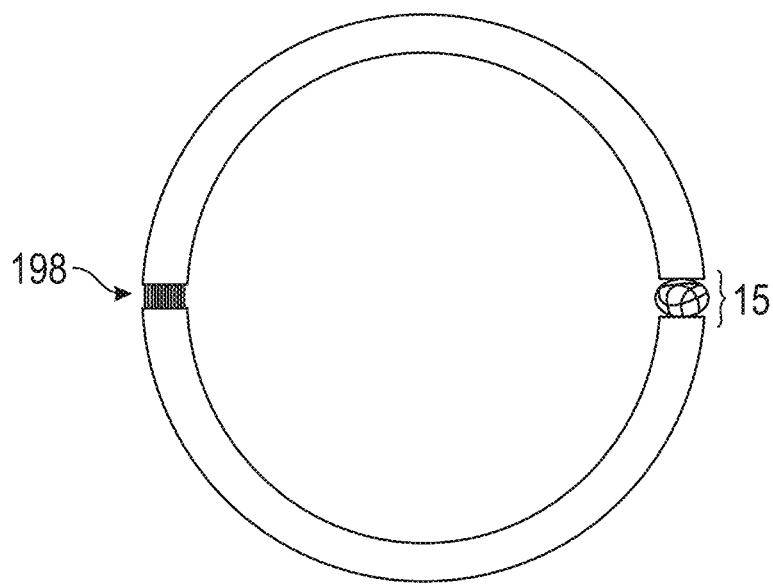
FIG. 36 illustrates an example gastroesophageal reflux treatment device with a gastroesophageal reflux preventer having a bangle preventer, in accordance with various embodiments.
Figure 37:
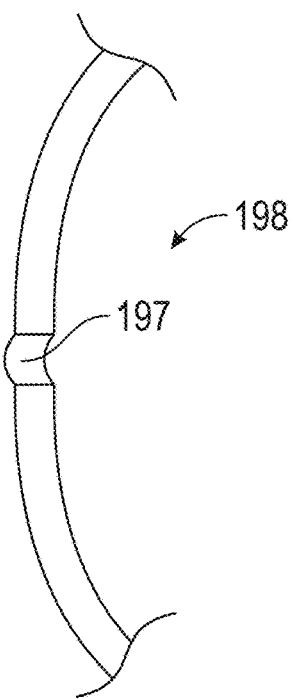
FIG. 37 illustrates an example bendable section of a bangle preventer, in accordance with various embodiments.
Figure 38:
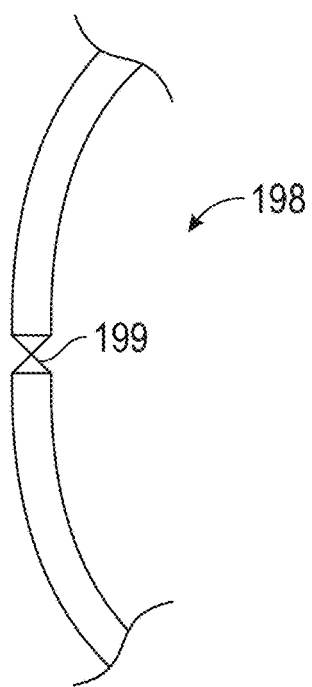
FIG. 38 illustrates an example hinged section of a bangle preventer, in accordance with various embodiments.
Figure 39:
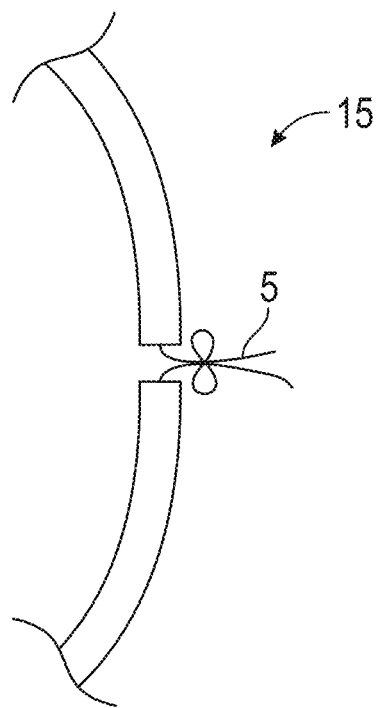
FIG. 39 illustrates an example closure mechanism of a bangle preventer including a knot, in accordance with various embodiments.
Figure 40:
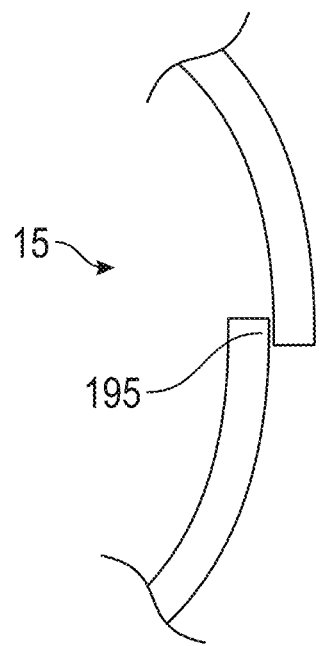
FIG. 40 illustrates an example closure mechanism of a bangle preventer including an abutment closure, in accordance with various embodiments.

With reference to FIG. 31, a gastroesophageal reflux preventer 6 comprising a braided multi-strand preventer 160 is provided. A gastroesophageal reflux preventer 6 may include an elongate portion configured as a braided multi-strand preventer 160. The braided multi-strand preventer 160 may comprise multiple strands of absorbable material that are braided together. In various instances, the multiple strands may be a same material as a support string 3 discussed elsewhere herein. The braided multi-strand preventer 160 may comprise a first strand 161-1, a second strand 161-2, and any number N of strands, such as an $N^{th}$ strand 161-n. A support string 3 may, in various embodiments, be omitted.

With reference to FIGS. 32-35, gastroesophageal reflux preventer 6 comprising an elongate portion configured as a chain-link preventer 180 is provided. The chain-link preventer 180 may comprise multiple links of absorbable material that are joined as a chain. The links may have different shapes. For example, a link may be round, such as a round link 182, or may be elliptical or otherwise stretched as a stretched link 184, or may be trapezoidal, as a trapezoidal link 186, or may be any shape as desired. For instance, the links may be herringbone, Figaro, ball, belcher, trace, box, snake, curb, wheat link, rope, rolo, popcorn, or any link style as desired.

Finally, and with reference to FIGS. 36-40, a gastroesophageal reflux preventer 6 comprising an elongate portion configured as a bangle preventer 190 is provided. A bangle preventer 190 comprises a first portion 192 comprising a curved member of absorbable material and a second portion 194 comprising a curved member of absorbable material, the first portion 192 and the second portion 194 joined by a flexible portion 198. The flexible portion 198 further may comprise absorbable material. For instance, a score line of the first portion 192 and/or the second portion 194 may facilitate a bending of the first portion 192 and second portion 194 relative to each other, thereby providing the flexible portion 198. In various embodiments, flexible portion 198 comprises a bendable section 197 such as may have a greater flexibility and/or elasticity than at least one of the first portion 192 and/or second portion 194. In further embodiments, flexible portion 198 comprises a hinge 199, so that at least one of the first portion 192 and the second portion 194 may be pivoted.

The first portion 192 and the second portion 194 may be joinable together by a closure mechanism 15. In various embodiments, the closure mechanism 15 comprises an abutment closure 195. For instance, the first portion 192 and the second portion 194 may at least partially abut proximate to an end of the first portion 192 and an end of the second portion 194. The abutting region may be sutured together, or may be magnetically attracted together, or may comprise mechanically interlocking features, etc. In various embodiments, the flexible portion 198 is omitted and the bangle preventer 190 may further omit a closure mechanism 15, being retainable in place by rigidity and/or semi-rigidity, and/or by sutures.

Various benefits and advantages have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, and any elements that may cause any benefit or advantage to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

Systems, methods and apparatus are provided herein. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f), unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

The invention claimed is:

1. A gastroesophageal reflux preventer that is generally elongated in shape, the gastroesophageal reflux preventer comprising:
    a first end;
    a second end;
    an elongate portion positioned between the first end and the second end and defining a longitudinal axis, the elongate portion comprising a plurality of nodes that are spaced apart along at least a portion of the length of the elongate portion;
    a first coupling portion; and
    a second coupling portion provided by two or more nodes of the plurality of nodes of the elongate portion, the two or more nodes of the second coupling portion each having an aperture defining an opening at least partially through the two or more nodes such that the opening is configured to couple with the first coupling portion;
    wherein the gastroesophageal reflux preventer may be provided in an uncoupled state and in a coupled state, and when in the coupled state the first coupling portion and the second coupling portion of the two or more nodes are coupled such that the elongate portion is at least partially curved and defines an enclosed area,
    wherein the first coupling portion engageable with one of a first node of the two or more nodes of the second coupling portion and a second node of the two or more nodes of the second coupling portion, and
    wherein the gastroesophageal reflux preventer is configured to be positioned around an outer surface of a body organ to retain at least a portion of the elongate portion in contact with an outer body tissue of the body organ during at least a portion of a scarification of the outer body tissue.

2. The gastroesophageal reflux preventer according to claim 1, wherein at least one suture stitches at least one of (i) the portions of the elongate portion between the plurality of nodes, and (ii) at least one of the plurality of nodes to the outer body tissue.

3. The gastroesophageal reflux preventer according to claim 1, wherein the first coupling portion comprises a tab formed from the first end of the elongate portion, and the openings of the second coupling portion comprise a slotted receiver configured to receive the tab to couple the first and second coupling portions in a coupled state.

4. The gastroesophageal reflux preventer according to claim 1, wherein the elongate portion comprises a sectioned tubular portion having a plurality of sections spaced apart along a length of the elongate portion.

5. The gastroesophageal reflux preventer according to claim 1, wherein the elongate portion is pre-formed to have a curved shape and at least partially retain the pre-formed curved shape after being sutured to the body tissue.

6. The gastroesophageal reflux preventer according to claim 1, wherein the elongate portion comprises a tube.

7. The gastroesophageal reflux preventer of claim 1, wherein the second coupling portion comprises two or more nodes.

8. The gastroesophageal reflux preventer of claim 7, wherein a first node of the two or more nodes of the second coupling portion is positioned adjacent to the second end.

9. The gastroesophageal reflux preventer of claim 1 wherein the openings of the second coupling portion are not aligned with the longitudinal axis of the elongate portion.

10. The gastroesophageal reflux preventer of claim 1 wherein the openings of the second coupling portion are substantially perpendicular to the longitudinal axis of the elongate portion.

11. The gastroesophageal reflux preventer of claim 1 wherein the gastroesophageal reflux preventer exerts an inward force on the outer surface of the body organ when positioned around the outer surface in the coupled state.

12. A gastroesophageal reflux preventer configured to be positioned around the exterior of a body organ, the gastroesophageal reflux preventer comprising:
    a support member;
    a plurality of nodes linked together by the support member, wherein at least one node of the plurality of nodes is formed of a material absorbable by a body tissue when placed in contact with the body tissue, the material selected such that the absorption of the material by the body tissue creates scarification adjacent the contact;
    a closure mechanism comprising a first coupling portion, and a second coupling portion configured to couple with the first coupling portion, wherein the second coupling portion is provided by one or more nodes of the plurality of nodes; and
    a suture portion configured to receive a suture to retain at least a portion of the gastroesophageal reflux preventer in contact with a tissue of the body organ;
    wherein, when the second coupling portion is coupled with the first coupling portion, the gastroesophageal reflux preventer defines an enclosed area when positioned around the body organ, and wherein the support member has a curved shape that is at least partially formable into a formed shape to at least partially correspond to a shape of the body tissue, and configured to at least partially retain the formed shape that at least partially corresponds to the shape of the body tissue after being sutured to the body tissue.

13. The gastroesophageal reflux preventer according to claim 12, wherein the closure mechanism is configured to further retain at least a portion of the plurality of nodes in contact with the body tissue during at least a portion of the scarification of the body tissue in response to absorption by the body tissue of at least one node of the plurality of nodes.

14. The gastroesophageal reflux preventer according to claim 12, wherein a plurality of nodes extend no more than 270 degrees around a portion of the body organ that includes the body tissue.

15. The gastroesophageal reflux preventer of claim 12, wherein the suture portion is a portion of one of the plurality of nodes.

16. The gastroesophageal reflux preventer of claim 12, wherein the suture portion is a portion of the support member.

17. A gastroesophageal reflux preventer comprising:
    an elongate portion comprising a pre-formed curved shape that is at least semi-rigid and having a first end and a second end that is opposite the first end of the pre-formed curved shape;
    a closure mechanism comprising a first closure portion positioned toward the first end, and a second closure portion positioned toward the second end, and wherein the first closure portion is configured to mechanically engage at least a portion of the second closure portion;
    wherein the elongate portion is formed of an absorbable material selected to induce scaring in a body organ when the material is absorbed by the body organ, wherein the gastroesophageal reflux preventer is configured to be secured to the exterior surface of the body organ in a closed position through at least the closure mechanism to allow one or more portions of the elongate portion to be in contact with the exterior surface of the body organ, and wherein, when secured to the exterior surface of the body organ in the closed position, the gastroesophageal reflux preventer provides sufficient inward force to maintain at least a portion of the gastroesophageal reflux preventer in contact with the exterior surface of the body organ.

18. The gastroesophageal reflux preventer of claim 17, wherein, when the gastroesophageal reflux preventer is secured in the closed position, the pre-formed curved shape comprises an arc-length of less than about 270 degrees.

19. The gastroesophageal reflux preventer of claim 17, wherein, when the gastroesophageal reflux preventer is secured in the closed position, the pre-formed curved shape comprises an arc-length of less than about 180 degrees.

20. The gastroesophageal reflux preventer of claim 17, wherein the pre-formed curved shape is emplaceable proximate to a gastroesophageal sphincter of a body part and emplaceable around a portion of the body part.

21. The gastroesophageal reflux preventer of claim 17, further comprising a first suture and a second suture, both sutures to retain at least a portion of the elongate portion in contact with a body part during at least a portion of a scarification of the body part in response to absorption by the body part of the elongate portion, wherein the first suture is disposed adjacent the first end of the curved shape and wherein the second suture is disposed adjacent the second end of the curved shape.

22. The gastroesophageal reflux preventer of claim 17, further comprising a suture portion configured to receive a suture to retain at least a portion of the elongate portion in contact with a tissue of the body organ, and wherein the suture portion is disposed between the first end of the curved shape and the second end of the curved shape, and the pre-formed curved shape at least partially retains its shape following emplacement at the body part.

23. A gastroesophageal reflux preventer that is generally elongated in shape, the gastroesophageal reflux preventer comprising:

an elongate portion formed of an inelastically deformable material and defining a length; and a plurality of nodes extending from the elongate portion in a spaced-apart configuration along the length of the elongate portion; wherein the gastroesophageal reflux preventer is configured to be positioned around at least a portion of an outer surface of a body tissue using sutures such that at least two of the plurality of nodes extending from the elongate portion are in contact with the outer surface of the body tissue, and wherein when the gastroesophageal reflux preventer positioned around at least a portion of an outer surface of a body tissue, the elongated portion is deformable to at least partially conform the elongated portion to the shape of the outer surface of the body tissue, and wherein the plurality of nodes are formed of an absorbable material selected to induce scarification of the body by the absorption by the body tissue of the at least two of the plurality of nodes that are in contact with the outer surface of the body tissue.

24. The gastroesophageal reflux preventer of claim 23, wherein the elongate portion is formed of an absorbable material.

25. The gastroesophageal reflux preventer of claim 23, wherein the elongate portion is formed of the same material as the plurality of nodes.

26. The gastroesophageal reflux preventer of claim 23, wherein the plurality of nodes are formed as part of the elongate portion.

* * * * *